(12) United States Patent
Lin

(10) Patent No.: US 11,559,622 B2
(45) Date of Patent: Jan. 24, 2023

(54) DEFORMATION RESISTANT WOUND THERAPY APPARATUS AND RELATED METHODS OF USE

(71) Applicant: Edward D. Lin, Osprey, FL (US)

(72) Inventor: Edward D. Lin, Osprey, FL (US)

(*) Notice: Subject to any disclaimer, the term of this patent is extended or adjusted under 35 U.S.C. 154(b) by 518 days.

(21) Appl. No.: 15/663,708

(22) Filed: Jul. 29, 2017

(65) Prior Publication Data

US 2019/0030225 A1 Jan. 31, 2019

(51) Int. Cl.
*A61M 1/00* (2006.01)
*A61F 13/02* (2006.01)
(Continued)

(52) U.S. Cl.
CPC ......... *A61M 1/90* (2021.05); *A61F 13/00068* (2013.01); *A61F 13/0206* (2013.01);
(Continued)

(58) Field of Classification Search
CPC .. A61M 1/001; A61M 1/0003; A61M 1/0027; A61M 1/0031; A61M 1/0037;
(Continued)

(56) References Cited

U.S. PATENT DOCUMENTS 2,280,915 A 4/1942 Johnson
3,026,874 A 3/1962 Stevens
(Continued)

FOREIGN PATENT DOCUMENTS

CN 102008373 A 4/2011
CN 101969902 B 2/2013
(Continued)

OTHER PUBLICATIONS

"BASF: Superabsorbent Fabric Keeps Feet Dry in All Weathers; Luquafleece from BASF in the IQ-Text Ventilation Element Clams Up in Tight in Wet Conditions," Oct. 7, 2008 (Year: 2008).*
(Continued)

*Primary Examiner* — Justine R Yu
*Assistant Examiner* — Benjamin M. Kusiak
(74) *Attorney, Agent, or Firm* — Cardle Patent Law Chtd

(57) ABSTRACT

The wound therapy apparatus may include a wound interface sealingly securable to the skin surface around a wound bed to encloses the wound bed within an enclosed space that is fluid-tight. The wound interface may be sufficiently deformation resistant to distend at least a portion of the wound bed into the enclosed space when pressure $p_0$ within the enclosed space is less than ambient pressure $p_{amb}$. Fluid may be communicated with the enclosed space when the wound interface is sealingly secured to the skin surface in order to vary a pressure $p_0$ within the enclosed space periodically over the pressure range $p_{min} \leq p_0 \leq p_{max}$. The variation of the pressure $p_0$ may distend the wound bed into communication with a pad received within the enclosed space and decreases the wound bed contact with the pad. Related methods of use of the wound therapy apparatus are also disclosed.

23 Claims, 19 Drawing Sheets

(51) Int. Cl.
- *A61H 7/00* (2006.01)
- *A61L 15/24* (2006.01)
- *A61L 15/26* (2006.01)
- *A61L 15/42* (2006.01)
- *A61F 13/00* (2006.01)

(52) U.S. Cl.
CPC ......... *A61F 13/0216* (2013.01); *A61H 7/001* (2013.01); *A61L 15/24* (2013.01); *A61L 15/26* (2013.01); *A61L 15/42* (2013.01); *A61F 2013/00182* (2013.01); *A61M 1/75* (2021.05); *A61M 1/82* (2021.05); *A61M 1/964* (2021.05); *A61M 2205/075* (2013.01); *A61M 2205/3331* (2013.01); *A61M 2205/3337* (2013.01); *A61M 2205/50* (2013.01); *A61M 2205/7536* (2013.01)

(58) Field of Classification Search
CPC .. A61M 1/0072; A61M 1/0088; A61M 1/009; A61M 1/0092; A61M 2202/0014; A61M 2202/04; A61M 2205/071; A61M 2205/075; A61M 2205/3331; A61M 2205/3337; A61M 2205/50; A61M 2205/502; A61M 2205/7536; A61L 15/24; A61L 15/26; A61L 15/42; A61F 13/00; A61F 13/00068; A61F 13/0206; A61F 13/0216; A61F 13/505; A61F 2013/0017; A61F 2013/00174; A61F 2013/00182
USPC ...................................................... 601/6–11
See application file for complete search history.

(56) References Cited

U.S. PATENT DOCUMENTS

| | | | |
|---|---|---|---|
| 3,300,786 A | 1/1967 | Rosenvold et al. | |
| 4,328,799 A | 5/1982 | LoPiano | |
| 4,399,816 A | 8/1983 | Spangler | |
| 4,635,618 A * | 1/1987 | Munz | A61H 9/005 601/6 |
| 5,086,763 A | 2/1992 | Hathman | |
| 5,154,697 A | 10/1992 | Loor | |
| D364,679 S | 11/1995 | Heaton et al. | |
| 5,522,794 A | 6/1996 | Ewall | |
| 5,562,107 A | 10/1996 | Lavender | |
| 5,607,388 A | 3/1997 | Ewall | |
| 5,636,643 A | 6/1997 | Argenta et al. | |
| 5,667,502 A | 9/1997 | Holtermann | |
| 5,769,806 A | 6/1998 | Radow | |
| 5,792,090 A | 8/1998 | Ladin | |
| 5,899,207 A | 5/1999 | Scheinberg | |
| 5,980,497 A | 11/1999 | Yavitz | |
| 6,062,215 A | 5/2000 | Leininger et al. | |
| 6,098,628 A | 8/2000 | Funk | |
| 6,142,982 A | 11/2000 | Hunt et al. | |
| 6,222,090 B1 | 4/2001 | Weston | |
| 6,328,709 B1 * | 12/2001 | Hung | A61B 5/4312 604/514 |
| 6,458,109 B1 | 10/2002 | Henley et al. | |
| 6,484,716 B1 | 11/2002 | Leininger et al. | |
| D469,175 S | 1/2003 | Hall et al. | |
| 6,553,998 B2 | 4/2003 | Heaton et al. | |
| D475,134 S | 5/2003 | Randolph | |
| 6,695,823 B1 | 2/2004 | Lina et al. | |
| D488,588 S | 4/2004 | Hall | |
| 6,764,462 B2 | 7/2004 | Risk et al. | |
| 6,767,334 B1 | 7/2004 | Randolph | |
| 6,767,344 B2 | 7/2004 | Suzuki | |
| 6,814,079 B2 | 11/2004 | Heaton et al. | |
| 6,824,533 B2 | 11/2004 | Risk, Jr. et al. | |
| 6,856,821 B2 | 2/2005 | Johnson | |
| 6,936,037 B2 | 8/2005 | Bubb et al. | |
| 6,951,553 B2 | 10/2005 | Bubb et al. | |
| 7,108,683 B2 | 9/2006 | Zamierowski | |
| 7,154,017 B2 | 12/2006 | Sigurjonsson et al. | |
| 7,532,953 B2 | 5/2009 | Vogel | |
| 7,534,240 B1 | 5/2009 | Johnson | |
| 7,608,066 B2 | 10/2009 | Vogel | |
| 7,790,945 B1 | 9/2010 | Watson, Jr. | |
| 7,837,673 B2 | 11/2010 | Vogel | |
| 7,909,805 B2 | 3/2011 | Weston | |
| 7,964,766 B2 | 6/2011 | Blott et al. | |
| D642,594 S | 8/2011 | Mattson et al. | |
| D648,353 S | 11/2011 | Mattson et al. | |
| 8,080,702 B2 | 12/2011 | Blott et al. | |
| 8,142,405 B2 | 3/2012 | Vogel | |
| 8,187,237 B2 | 5/2012 | Seegert | |
| 8,529,532 B2 * | 9/2013 | Pinto | A61F 13/00029 604/319 |
| 8,563,604 B2 | 10/2013 | Palefsky et al. | |
| 8,708,982 B2 | 4/2014 | Lin | |
| 8,821,419 B1 * | 9/2014 | Van Beek | A61B 90/02 601/6 |
| 9,913,757 B2 * | 3/2018 | Vitaris | A61F 13/00063 |
| 9,925,361 B2 | 3/2018 | Lin | |
| 2001/0029956 A1 | 10/2001 | Argenta | |
| 2001/0041188 A1 | 11/2001 | Gibbins et al. | |
| 2002/0017304 A1 | 2/2002 | Heaton et al. | |
| 2002/0143286 A1 | 10/2002 | Tumey | |
| 2002/0155164 A1 | 10/2002 | Figley | |
| 2003/0014022 A1 | 1/2003 | Lockwood | |
| 2003/0021775 A1 | 1/2003 | Freeman | |
| 2003/0040687 A1 | 2/2003 | Boynton et al. | |
| 2003/0050594 A1 | 3/2003 | Zamierowski | |
| 2003/0212357 A1 | 11/2003 | Pace | |
| 2003/0219469 A1 | 11/2003 | Johnson et al. | |
| 2004/0006319 A1 | 1/2004 | Lina et al. | |
| 2004/0010207 A1 | 1/2004 | Flaherty et al. | |
| 2004/0030304 A1 * | 2/2004 | Hunt | A61F 13/0216 604/317 |
| 2004/0073151 A1 | 4/2004 | Weston | |
| 2004/0093026 A1 | 5/2004 | Weidenhagen et al. | |
| 2004/0153032 A1 | 8/2004 | Garribotto et al. | |
| 2004/0170703 A1 | 9/2004 | Hoekstra et al. | |
| 2005/0137521 A1 | 6/2005 | Stenzler | |
| 2005/0220849 A1 | 10/2005 | Hickey | |
| 2005/0228340 A1 | 10/2005 | Cleary | |
| 2006/0127462 A1 * | 6/2006 | Canada | A01N 59/16 424/445 |
| 2006/0146234 A1 | 7/2006 | Bear et al. | |
| 2006/0185670 A1 | 8/2006 | Loori et al. | |
| 2007/0041960 A1 | 2/2007 | Freeman et al. | |
| 2007/0118096 A1 | 5/2007 | Smith | |
| 2007/0265586 A1 * | 11/2007 | Joshi | A61M 1/0035 604/313 |
| 2008/0140029 A1 | 6/2008 | Smith et al. | |
| 2009/0258058 A1 | 10/2009 | Thomas et al. | |
| 2009/0312723 A1 | 12/2009 | Blott et al. | |
| 2010/0069858 A1 * | 3/2010 | Olson | A61F 13/00987 604/319 |
| 2010/0268128 A1 * | 10/2010 | Randolph | A61F 13/00068 601/6 |
| 2010/0298792 A1 | 11/2010 | Weston et al. | |
| 2011/0160686 A1 | 6/2011 | Ueda et al. | |
| 2012/0029449 A1 * | 2/2012 | Khosrowshahi | A61M 1/0088 604/321 |
| 2012/0316538 A1 * | 12/2012 | Heiser | A61M 1/90 604/543 |
| 2013/0053795 A1 * | 2/2013 | Coulthard | A61F 13/00055 604/319 |
| 2013/0165837 A1 | 6/2013 | Addison et al. | |
| 2013/0211318 A1 | 8/2013 | Croizat et al. | |
| 2013/0231623 A1 | 9/2013 | Richard | |
| 2013/0303975 A1 | 11/2013 | Gvodas, Jr. | |
| 2014/0155790 A1 * | 6/2014 | Argenta | A61M 1/0037 601/6 |
| 2014/0207027 A1 * | 7/2014 | Navia | A61F 13/00068 604/319 |
| 2014/0309574 A1 | 10/2014 | Cotton | |
| 2015/0005678 A1 * | 1/2015 | Wall | A61M 1/0084 601/9 |

(56) References Cited

U.S. PATENT DOCUMENTS

| | | | |
|---|---|---|---|
| 2015/0088085 A1 | 3/2015 | Rovaniemi | |
| 2015/0216733 A1* | 8/2015 | Allen | A61F 13/00059 |
| | | | 604/319 |
| 2016/0038626 A1* | 2/2016 | Locke | A61L 15/425 |
| | | | 601/6 |
| 2016/0074232 A1* | 3/2016 | Vitaris | A61F 13/00046 |
| | | | 604/319 |
| 2016/0128894 A1* | 5/2016 | Horton | A61H 9/0057 |
| | | | 601/11 |
| 2016/0166781 A1 | 6/2016 | Sarangapani et al. | |
| 2016/0256665 A1 | 9/2016 | Doshi et al. | |
| 2016/0262944 A1 | 9/2016 | Shmuelovitch et al. | |
| 2017/0007751 A1* | 1/2017 | Hartwell | A61F 13/0206 |
| 2017/0119940 A1 | 5/2017 | Quisenberry | |
| 2018/0169395 A1 | 6/2018 | Lin | |
| 2019/0029886 A1 | 1/2019 | Lin | |
| 2019/0030223 A1 | 1/2019 | Lin | |
| 2019/0030224 A1 | 1/2019 | Lin | |
| 2019/0030225 A1 | 1/2019 | Lin | |
| 2019/0030226 A1 | 1/2019 | Lin | |
| 2019/0133830 A1* | 5/2019 | Bishop | A61F 13/0216 |
| 2019/0151156 A1* | 5/2019 | Kieswetter | A61F 13/00068 |

FOREIGN PATENT DOCUMENTS

| | | |
|---|---|---|
| CN | 102985096 A | 3/2013 |
| CN | 104024498 A | 9/2014 |
| CN | 106659590 A | 5/2017 |
| EP | 0206646 | 12/1986 |
| EP | 0940131 A2 | 9/1999 |
| EP | 1219311 | 7/2004 |
| EP | 1018967 | 8/2004 |
| EP | 1674898 | 6/2006 |
| EP | 1901686 | 7/2014 |
| EP | 2995324 A1 | 3/2016 |
| EP | 3156016 | 4/2017 |
| GB | 288220 | 8/1928 |
| GB | 2265314 | 9/1993 |
| GB | 2329127 | 3/1999 |
| GB | 2351025 | 12/2000 |
| GB | 2365350 | 2/2002 |
| GB | 2496310 B | 10/2015 |
| WO | 9605873 | 2/1996 |
| WO | 0059418 | 10/2000 |
| WO | 0059424 | 10/2000 |
| WO | 03049660 | 6/2003 |
| WO | 2003092620 | 11/2003 |
| WO | 2004060148 | 7/2004 |
| WO | 2005009488 | 2/2005 |
| WO | 2005046761 A1 | 5/2005 |
| WO | 2006081403 A1 | 8/2006 |
| WO | 2009141820 A1 | 11/2009 |
| WO | 2011130246 A2 | 10/2011 |
| WO | 2013066694 A2 | 5/2013 |
| WO | 2013123005 A1 | 8/2013 |
| WO | 2015193257 A1 | 12/2015 |
| WO | 2019027806 A1 | 2/2019 |
| WO | 2019027807 A1 | 2/2019 |
| WO | 2019027808 A1 | 2/2019 |
| WO | 2019027809 A1 | 2/2019 |
| WO | 2019027810 A1 | 2/2019 |

OTHER PUBLICATIONS

Pawlaczyk M, Lelonkiewicz M, Wieczorowski M. Age-dependent biomechanical properties of the skin. Postepy Dermatol Alergol. 2013;30(5):302-306. doi:10.5114/pdia.2013.38359 (Year: 2013).*
Vinidex, "PVC Properties," accessed from URL: https://www.vinidex.com.au/technical-resources/material-properties/pvc-properties/ (Year: 2022).*
Merriam Webster, "Definition of Rigid" (Year: 2022).*
International Search Report for International Application No. PCT/US2018/043953 dated Oct. 9, 2018.
International Search Report for International Application No. PCT/US2018/043955 dated Oct. 17, 2018.
International Search Report for International Application No. PCT/US2018/043957 dated Oct. 19, 2018.
International Search Report for International Application No. PCT/US2018/043959 dated Oct. 15, 2018.
International Search Report for International Application No. PCT/US2018/043962 dated Oct. 16, 2018.
Cardinal Health NPWT Pro Family, Cardinal Health, Waukegan, IL, 2015.
Cardinal Health SVED Clinician User Manual, Cardinal Health, Waukegan, IL, 2015.
Cardinal Health SVED Wound Care Anywhere, Cardinal Health, Waukegan, IL, 2015.
Cardinal Health SVED Clinician Quick Reference Guide, Cardinal Health, Waukegan, IL, 2015.
Cardinal Health SVED Patient User Manual, Cardinal Health, Waukegan, IL, 2015.
ITI Brings Hospitals New Value Model For Wound Care, Innovative Therapies, Inc. Copyright 2013 PR Newswire.
Application Guide: Pico multisite with softport technology applied to the heel, PCPE-48-0717-UE, Smith & Nephew, Inc. 2017.
Avance® Clinician's Guidelines, Revision Feb. 2017, Mölnlycke Health Care US, LLC, Norcross, GA 30092.
Borgquist, O., R. Ingemansson, M Malmsjö, Effects of negative pressure wound therapy on regional blood flow, wound contraction and fluid removal—Examining low pressure levels, intermittent and variable therapy, 24th Annual Clinical Symposium on Advances in Skin & Wound Care, San Antonio, Texas, USA—Oct. 22-25, 2009.
Borgquist, Ola, et al. Wound Edge Microvascular Blood Flow during Negative-Pressure Woulnd Therapy: Examining the Effects of Pressures from -10 to -175 mmHg, PRSJournal, vol. 125, No. 2, 2010, 502-509.
Cardinal Health Sved, "Clinician Quick Reference Guide", Cardinal Health, the Netherlands, 2015, 2 pages.
Chanden K. Sen, Wound healing essentials: Let there be oxygen, Wound Rep Reg (2009) 17 1-18.
Eriksson, et al., Wet wound healing: from laboratory to patients to gene therapy, The American Journal of Surgery 188 (Suppl to Jul. 2004) 36S-41S.
EZCare Negative Pressure Wound Therapy, V1STA Negative Pressure Wound Therapy, Negative Pressure Wound Therapy Clinical Guidelines, BS-0039-0808, Smith & Nephew.
Final Rejection, U.S. Appl. No. 15/663,710, filed Nov. 25, 2019.
Ghatak, Schlanger, Ganesh, Lambert, Gordillo, Martinsek,and Roy, A Wireless Electroceutical Dressing Lowers Cost of Negative Pressure Wound Therapy, Adv Wound Care (New Rochelle) 4(5): 302-311, May 2015.
Malsmjo, MD, et al., Negative pressure wound therapy using gauze or polyurethane open cell foam: similar effects on would edge microvascular blood flow, Lund University, 1 page.
Niederauer, Mark Q. et al. Continuous diffusion of oxygen improves diabetic foot ulcer healing when compared with a placebo control: a randomised, double-blind, multicentre study, J. Wound Care, N. American Supplement, vol. 27, No. 9, Sep. 2018.
Non Final Rejection, U.S. Appl. No. 15/663,710, filed Jul. 11, 2019.
Non-Final Rejection, U.S. Appl. No. 15/663,709, filed Oct. 10, 2019.
Non-Final Rejection, U.S. Appl. No. 15/663,713, filed Jun. 28, 2019.
Non-Final Rejection, U.S. Appl. No. 15/663,714, filed Sep. 13, 2019.
Notice of References Cited, U.S. Appl. No. 15/663,709.
Notice of References Cited, U.S. Appl. No. 15/663,710.
Notice of References Cited, U.S. Appl. No. 15/663,713.
Notice of References Cited, U.S. Appl. No. 15/663,714.
Prevena Incision Management System, Clinician Guide, 390061 Rev C, KCI Licensing Inc., 2009.
Prevena Incision Management System, Product Monograph, KCI Licensing Inc., 2010.
Prospers Negaitve Pressure Wound Therapy, Pro-I, Advancing the Art and Science of NPWT, Prospera, Ft. Worth, Tx, 2008. MR-125-04/08.

(56) References Cited

OTHER PUBLICATIONS

RENASYS Negative Pressure Wound Therapy, Pico Single Use Negative Pressure Wound Therapy System, NPCE-48-0613-NAE, Smith & Nephew, Inc., 2013.
V.A.C. Ulta Quick Reference Guide, KCI Licensing Inc., 2013.
V.A.C. Ulta™ Negative Pressure Wound Therapy System, KCI Licensing Inc., Apr. 17, 2016.

* cited by examiner

DEFORMATION RESISTANT WOUND THERAPY APPARATUS AND RELATED METHODS OF USE

CROSS-REFERENCE TO RELATED APPLICATIONS

This application hereby incorporates by reference in the entirety herein the co-pending U.S. patent application Ser. No. 15/663,709 entitled "AUGMENTED PRESSURE THERAPY FOR WOUNDS," U.S. patent application Ser. No. 15/663,710 entitled "CONTROL APPARATUS AND RELATED METHODS FOR WOUND THERAPY DELIVERY," U.S. patent application Ser. No. 15/663,713 entitled "WOUND COVER APPARATUS AND RELATED METHODS OF USE," and U.S. patent application Ser. No. 15/663,714 entitled "WOUND THERAPY APPARATUS WITH SCAR MODULATION PROPERTIES AND RELATED METHODS," all by Edward D. Lin as inventor and applicant and filed on 29 Jul. 2017.

BACKGROUND OF THE INVENTION

Field

The present disclosure relates to medical devices, and, more particularly, to apparatus and related methods for wound therapy.

Related Art

A wound bed, as used herein, includes a localized region of tissue that has been affected by hostile factors, resulting in, for example, cellular abnormality such as swelling, inflammation, degradation, infection, or cell death. The wound bed may include varying degrees of exposure of underlying layers and structures, along with possible infections and tissue changes. The wound bed represents an unhealed wound. In contrast, a healed wound is a skin surface that was previously injured but the focal breach is now entirely sealed and covered by varying amounts of epidermis and scar tissue. The wound bed may lie within a wound boundary that extends around the affected region at the skin surface of the skin. The wound bed may extend contiguously in depth within the dermis, and the wound bed may extend yet deeper, for example, into subcutaneous fat, and deeper structures. Thus, the wound bed may include undermined flaps, sinuses, tunnels, and fistulae and the surrounding affected tissues. An example of a complex wound bed including some reference anatomy is illustrated in FIG. 1. Wound boundary, as used herein, refers to the perimeter of the wound bed at the skin surface of the skin.

Wounds may take a long time to heal, for example, due to compromised circulation and hypoxia. A 2012 study based on the US Wound Registry analyzed reimbursement data on 5240 patients with 7099 wounds and determined the cost to treat 6.4 million wounds in the US to be a shocking $50 billion, more than twice the previous estimate and an expense that is 10× the budget of the WHO. 65.8% of wounds have an average healing time of 15 weeks and 10% of wounds taking 33 weeks or more to heal. Nearly 80,000 amputations occur annually in the US, and each amputation may represent many months, if not years, of failed costly therapy.

Current negative pressure wound therapy (NPWT) devices may include a dressing packed into the wound bed, a thin flexible sheet of generally fluid-impervious polymer that is adhesive coated on its underside, and an evacuation tube in fluid communication with the dressing. While the sheet in common clinical use is often referred to as "occlusive" or even "semi-permeable", it is understood that its permeability is generally limited to transpiration (allowing the skin to 'breathe') and not ready passage of fluids. The dressing, may be, for example, cotton gauze, or open-cell foam made from polyvinyl alcohol or polyurethane.

After the wound bed is packed with dressing, the sheet may be then centered over the dressing and wound bed, and then secured sealingly adhesively to the skin around the wound bed to seal the wound bed and dressing. Finally, an aperture is created in the sheet over the dressing, and a connector and evacuation tubing is sealingly engaged with that aperture. Air within the region between the sheet and the wound bed is evacuated through the tubing to produce a suction pressure $p_s$ within the region that is less than the ambient pressure $p_{amb}$. The wound bed and surrounding skin contract as the pressure within the region is decreased by suction pressure $p_s$ which causes ambient pressure to compresses the sheet and dressing upon the wound bed. Exudate from the wound bed may be drawn through the dressing and evacuated through the evacuation tube.

However, current NPWT devices suffer from various disadvantages. For example, the dressing must be trimmed to the exact geometry of wound bed as overlap of the dressing over normal skin may result in maceration of the normal skin. Undetected dressing fragments and trimming debris in the wound may create foci for infection. The dressing may require frequent changing, typically every other day, and each dressing change may be excruciating, so painful that a strong analgesic or local anesthetic may be required as premedication prior to the dressing change. Desirable granulation tissue may be drawn by suction pressure $p_s$ into the micro-crevices of the dressing, which is in constant contact with the wound bed, and the granulation tissue may be torn or damaged with each dressing change resulting in recurring setbacks in the healing process. Furthermore, dressing changes are costly in terms of time, medical personnel and consumables.

The suction pressure $p_s$ over the wound bed may be uneven as the suction pressure $p_s$ is transmitted through varying dressing thicknesses across varying distances from the evacuation tube. This uneven suction pressure distribution, as well as the uneven compression pressure from the same thickness dressing being forced into an uneven thickness wound bed may be important in the causation of well-documented diminished blood flow in the wound bed near the wound boundary of the wound bed. (See, for example, Borgquist, O., R. Ingemansson, M Malmsjö, *Effects of negative pressure wound therapy on regional blood flow, wound contraction and fluid removal—Examining low pressure levels, intermittent and variable therapy,* 24th Annual Clinical Symposium on Advances in Skin & Wound Care, San Antonio, Tex., USA—Oct. 22nd-25th, 2009). Such diminished blood flow within the wound boundary may impede healing of the wound bed because healing typically diminishes the wound bed from the periphery towards the center. For example, in wound beds with severe underlying vasculopathy such as may be found in advanced diabetes, current NPWT devices may not be able to increase blood flow sufficiently because the suction pressure $p_s$ compresses the capillaries in the wound bed, which works at cross purposes to the goal of increasing blood flow.

Drainage of the wound bed may also be problematic in current NPWT devices as the protein-rich exudate from the wound bed may be retained in the dressing and evacuation tube, often resulting in clogging of the suction system, false pressure readings and unrecognized cessation of NPWT therapy.

In addition, current NPWT devices may only be used after a wound is first cleaned and debrided, and also may not be usable during the terminal phase of wound healing, as the presence of the dressing, which acts as a foreign body in the wound bed, may prevent full closure of the wound bed.

Accordingly, there is a need for improved apparatus as well as related methods for wound therapy.

BRIEF SUMMARY OF THE INVENTION

These and other needs and disadvantages may be overcome by the wound therapy apparatus and related methods of use disclosed herein. Additional improvements and advantages may be recognized by those of ordinary skill in the art upon study of the present disclosure.

A wound therapy apparatus is disclosed herein. In various aspects, the wound therapy apparatus may include a wound interface sealingly securable to the skin surface around a wound bed to encloses a wound boundary of a wound bed within an enclosed space formed by the wound interface that is fluid-tight. The wound interface may be sufficiently deformation resistant to distend at least a portion of the wound bed into the enclosed space when pressure $p_0$ within the enclosed space is less than ambient pressure $p_{amb}$. The wound therapy apparatus may include a port disposed about the wound interface to communicate fluid with the enclosed space when the wound interface is sealingly secured to the skin surface in order to vary the pressure $p_0$ within the enclosed space periodically over the pressure range $p_{min} \leq p_0 \leq p_{max}$, in various aspects. The wound therapy apparatus may include a pad receivable within the enclosed space to absorb exudate emanating from the wound bed, in various aspects. The variation of the pressure $p_0$ distends the wound bed into communication with the pad received within the enclosed space and releases the wound bed from communication with the pad received in the enclosed space when the wound interface is sealingly secured to the skin surface around the wound bed, in various aspects. Related methods of use of the wound therapy apparatus are also disclosed herein.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

Figure 1:
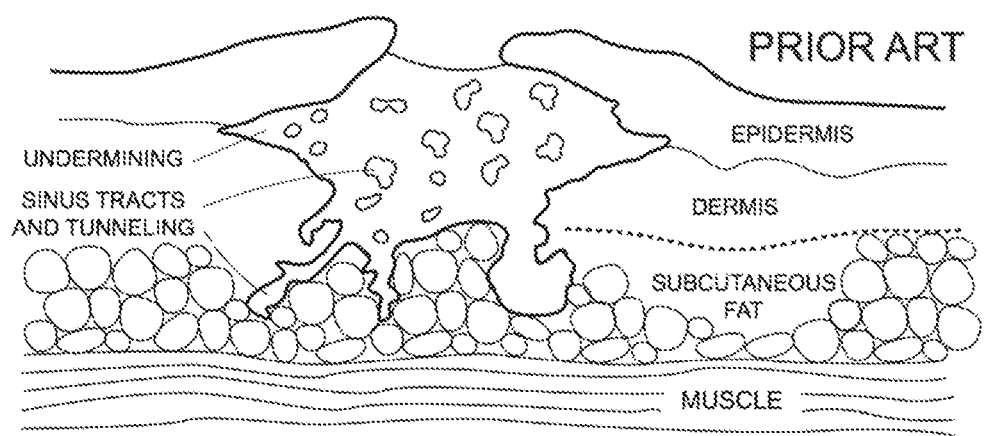
FIG. 1 by cross-sectional view an exemplary wound bed that has undermining, wound tunneling, and fistulae.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be readily recognized by those of ordinary skill in the art upon study of this disclosure.

DETAILED DESCRIPTION OF THE INVENTION

A wound therapy apparatus and related methods of use are disclosed herein. In various aspects, the wound therapy apparatus includes a wound interface sealingly securable to the skin surface around a wound bed to enclose portions of the wound bed at the skin surface by an enclosed space defined within the wound interface that is fluid-tight. The wound interface is sufficiently deformation resistant to accommodate distention of at least a portion of the wound bed into the enclosed space when the pressure $p_0$ within the enclosed space is less than ambient pressure $p_{amb}$, in various aspects. The wound interface may be functionally connected to other devices ranging from a manual suction source to a control module that monitors various parameters within the enclosed space and interacts with such parameters to deliver various therapies to the wound bed.

A pad is disposed in communication with the enclosed space to absorb exudate emanating from the wound bed, in some aspects. The wound therapy apparatus may include one or more ports that fluidly communicate with the enclosed space to periodically vary the pressure $p_0$ within the enclosed space over a pressure range $p_{min} \leq p_0 \leq p_{max}$ by flowing gaseous fluids into or out of the enclosed space through the one or more ports provided for that purpose. The time period over which the pressure $p_0$ is periodically varied may range from about 5 minutes (12 times per hour) to about 6 minutes (10 times per hour), in various aspects, or may be shorter or longer. Periodically varying the pressure $p_0$ within the enclosed space may massage the wound bed and surrounding tissue, for example, by alternately distending the wound bed into the enclosed space by suction pressure $p_0 < p_{amb}$ and releasing the wound bed from distention into the enclosed space to baseline state at $p_0 \approx p_{amb}$.

Exudate, as used herein, includes, for example, proteinaceous liquids exuded from the wound bed, along with various plasma and blood components. Exudate may also include other liquids used in treating the wound bed.

Fluid, as used herein, includes, liquid(s), gas(ses), and combinations thereof. Liquid may include, for example, saline solution, proteolytic enzyme solutions, antimicrobial lavages, amniotic fluid, and exudate. Gas may include, for example, air, oxygen, nitric oxide, nitrogen, therapeutic or inert gasses, and combinations thereof.

In various aspects, the term fluid-tight or related terms, as used herein, means sufficiently leak-resistant to allow insufflation or vacuum suction to create pressure $p_0$ within the enclosed space that may be above or below ambient pressure $p_{amb}$. The term fluid-tight means sufficiently leak-resistant to substantially retain fluids including both gasses and liquids within the enclosed space other than by controlled fluid communication through one or more lumen that fluidly communicate through the wound interface with the enclosed space, in certain aspects. In certain aspects, fluid tight means sufficiently leak-resistant to maintain pressure $p_0$ within the enclosed space that may be above or below ambient pressure $p_{amb}$.

Ambient pressure $p_{amb}$, as used herein, refers to the pressure in a region surrounding the wound therapy apparatus. Ambient pressure $p_{amb}$, for example, may refer to atmospheric pressure, hull pressure within an aircraft or submarine where the wound therapy apparatus is being utilized, or pressure maintained generally within a building or other structure where the wound therapy apparatus is being utilized. Ambient pressure $p_{amb}$ may vary, for example, with elevation or weather conditions. Pressure $p_{min}$ refers to the minimum pressure achieved within the enclosed space of the wound therapy apparatus, and periodically varying of pressure $p_0$, pressure variation, varying pressure, and similar term refer to changes of pressure $p_0$ within the enclosed space over time. Pressure $p_{max}$ refers to the maximum pressure achieved within the enclosed space of the wound therapy apparatus.

Pad, as used herein, may include a range of absorbent materials that absorb exudate including open-cell foam composed, for example, of polyvinyl alcohol (PVA), polyurethane or other polymer foam. The pad may include various fibers such as sodium carboxymethyl cellulose hydrofiber (Aquacel®), or a nonwoven fabric comprised of multi-component fibers of nylon and polyester that have been longitudinally split into their individual components by hydroentanglement (Evolon®). The pad may include knitted fibers, such as in the jersey-knit pattern with hydrophobic fibers predominant on outer surface and hydrophilic fibers predominantly on the inside to serve as a conduit to fluid transfer. The pad may also include non-knitted fibers that have been co-wound, cross-laid and/or twisted together into suitable shapes, such as cylinders or ribbons of various sizes and thicknesses, wherein numerous linear passageways are created between fibers to conduct liquid by capillary action. The hydrophobic fiber may be formed of a polyester, and the hydrophilic fiber may be formed of aliphatic polyamide fiber or semi-aromatic polyamide fiber (e.g. Nylon®). A polyester-polyurethane copolymer fiber (e.g. Spandex® or Lycra®) may additionally be incorporated in the weave to lend stretchability and conformity to the pad. The hydrophobic fibers may wick away liquid to prevent moisture buildup and, thus, maceration of tissue with which it is in contact. The hydrophilic fibers may promote wicking to help transmit the fluid towards the evacuation port of the wound interface.

As used herein, in various aspects, a wound interface that is deformation resistant maintains an enclosed space within sufficient to draw wound tissue towards the enclosed space, up to occupying the enclosed space, when subjected to pressure $p_0 \ll p_{amb}$, in various aspects. In various aspects, the wound interface is sufficiently deformation resistant to maintain the enclosed space resulting in distention of at least a portion of the wound bed towards or into the enclosed space by a pressure $p_0$ within the enclosed space that is less than ambient pressure $p_{amb}$. In various aspects, the wound interface is sufficiently deformation resistant to maintain the enclosed space over the wound bed, resulting in distention of at least a portion of the wound bed towards the enclosed space or into the enclosed space by a pressure $p_0$ within the enclosed space sufficiently below ambient pressure $p_{amb}$. In some aspects, at least portions of the wound interface that define the enclosed space may be essentially rigid. The wound interface, in various aspects, is sufficiently deformation resistant to remain sealingly secured to skin and fluid-tight over pressure range $p_{min} \leq p_0 \leq p_{max}$.

As used herein the terms distal and proximal are defined from the point of view of a healthcare provider, treating a patient with the wound therapy apparatus. When so treating the patient, a distal portion of the wound therapy apparatus is oriented toward the patient and a proximal portion of the wound therapy apparatus is oriented toward the physician. A distal portion of a structure is the portion closest to the patient while a proximal portion of the structure may be the portion closest to the physician.

Massaging of the wound bed via pressure variations, including rhythmic distortion of the wound bed volume, may be accompanied by fluxes of increased blood flow. The terms massage, massaging, rhythmic distortion, tissue deformation, distention of wound bed, may be used interchangeably in this disclosure to refer to the general process of subjecting the wound bed to pressure fluctuations and the resultant changes in the wound bed, including blood flow, oxygenation, cellular tension, macro- and micro-deformation and other changes. The surges of increased blood flow proximate the wound bed may bring increased nutrients and immunity elements, reduce infection and inflammation, and confer other beneficial effects that may promote healing of the wound bed. Massaging of the wound bed may promote the removal of exudate from the interstitial space of the wound bed to exit the wound crater. This may reduce capillary compression secondary to edema and improve the microcirculation to and within the wound. At least one of the one or more ports may fluidly communicate with the pad to allow transfer of exudate from the pad. Optionally, at least one of the one or more ports may be fluidly used for monitoring directly or indirectly parameters within the enclosed space such as pressure, temperature, humidity, pH, tissue oxygenation level, blood flow, etc. to effect improved therapy.

Figure 2A:
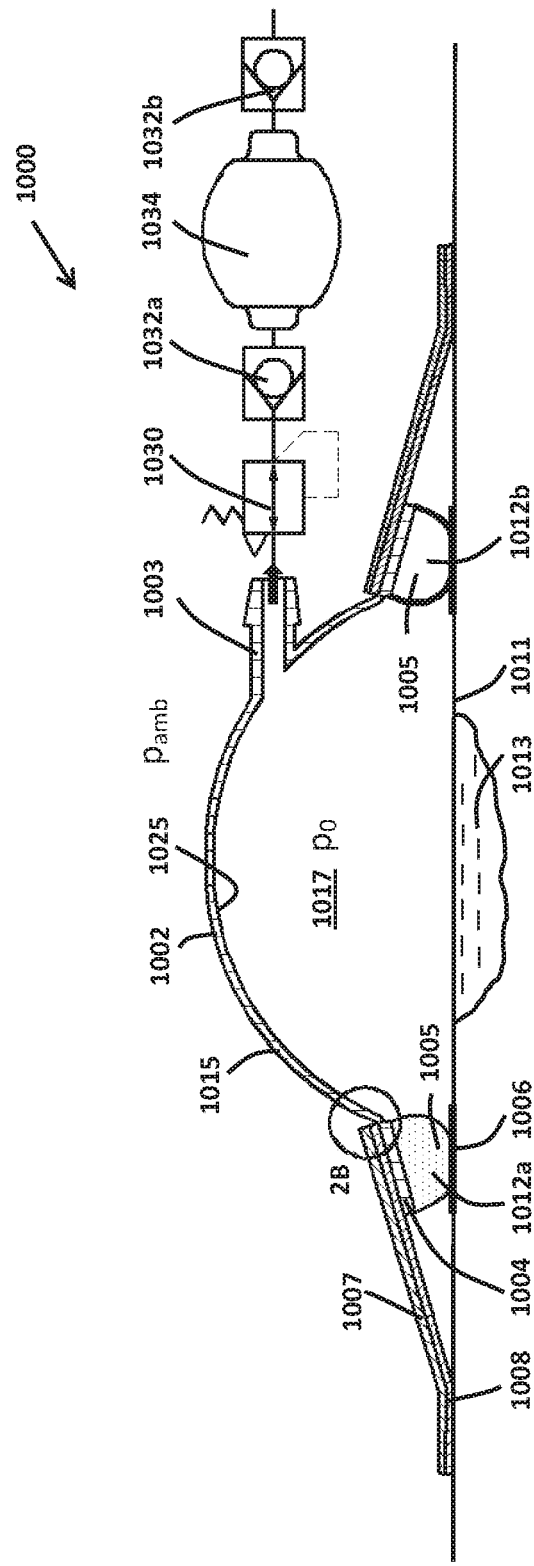
FIG. 2A illustrates by cross-sectional view an exemplary implementation of a wound therapy apparatus.
Figure 2B:
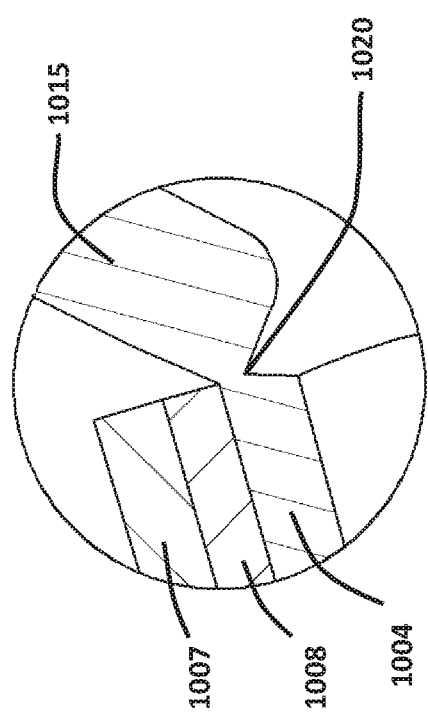
FIG. 2B illustrates by magnified cross-sectional view the circled area of the exemplary implementation of the wound therapy apparatus illustrated in FIG. 2A.

FIGS. 2A and 2B illustrates exemplary wound therapy apparatus 1000. As illustrated in FIG. 2A, wound therapy apparatus includes wound interface 1015 secured to the skin surface 1011 to enclose wound bed 1013 within enclosed space 1017 defined by wound interface 1015. As illustrated in FIG. 2A, wound interface 1015 includes cover 1002, which may have a range of transparency ranging from clear to opaque, an annular base flange 1004, and one or more ports, such as port 1003 emanating from the wound interface. The port(s) are optional, in this implementation, such as for wound protection and humidification. Port 1003 fluidly communicates with enclosed space 1017, as illustrated, and may be connected to tubing in communication with various fluid sources or fluid sinks for fluid communication between the fluid sources or fluid sinks and enclosed space 1017. Port 1003 may be used for monitoring directly or indirectly parameters within enclosed space 1017. Port 1003, for example, may be connected to a source such as a suction squeeze bulb 1034 illustrated in FIG. 2A in order to provide intermittent NPWT. Squeeze bulb 1034 may have one-way valves 1032a, 1032b to ensure unidirectional suction evacuation of the enclosed space. An optional relief valve 1030 may be incorporated into the wound interface 1015 or interposed between port 1003 and the bulb 1034 in order to limit the lowest suction pressure within the enclosed space. Port 1003 may be sealably open or closed by a variety of mechanism, including a self-sealing one-way valve 1032a as may be frequently used in medical applications. The suction bulb 1034 can similarly be equipped with a coupling tip to couple with valve 1032a to provide intermittent suction therapy such as may be needed in remote military missions or rural health settings.

The base flange 1004 is designed to be flexible, conformable, and pressure defusing diffusing, in this implementation. This may be achieved singularly or in combination in a variety of ways including base flange 1004 having a reduced thickness compared to the rest of the wound interface 1015, by molding or co-molding with a softer polymer, and/or by suitable structural modification to permit enhanced stretch and flexibility either diffusely or by sector.

FIG. 2B illustrates one implementation of this enhanced flexibility in which a living hinge 1020 is molded around the perimeter of base flange 1004. Not shown, but would be understood by one of ordinary skill in the art upon studying this disclosure, is to incorporate engineered sections of leaf membrane and increased elasticity dispersed in repeated sections or zones across the base flange 1004. The result is greater conformability to varying skin topography. Although the base flange 1004 may be directly secured to skin 1011 by adhesive, one implementation interposes between the base flange and skin, an optional annular cushion 1005 that may take the form of closed cell foam 1012a (as shown on the left side of FIG. 2A) or an air sac 1012b (as shown on the right side of FIG. 2A). In yet another exemplary variation of securing wound interface 1015 to the skin, an annular apron 1007 of suitable bandage material such as polyurethane with an undercoating of adhesive 1008, is adhered proximally to the base flange, and adhered distally to the skin to anchor the wound interface sealingly against skin 1011.

A pad, such as pad 50, 150, 450, 550, 650, may optionally be disposed in communication with the enclosed space 1017 to absorb exudate emanating from the wound bed, in various aspects. Cover 1002 forms a raised wound interface having a generally circular, rectangular or ovoid footprint, with a base flange 1004 that extends around the entire perimeter of cover 1002. Wound interface 1015 is sealed to skin surface 1011 by base flange 1004, and additionally but optionally cushion 1005 and adhesive 1006 or apron 1007 and adhesive 1006. Wound interface 1015 is essentially fluid-tight, as illustrated, and enclosed space 1017 completely encloses wound bed 1013. Interior pressure $p_0$ may be established by input or withdrawal of fluid into enclosed space 1017 or evacuation of fluid from enclosed space 1017 via port 1003. Pressure $p_0$ may be varied periodically generally over the pressure range $p_{min} \leq p_0 \leq p_{amb}$ to periodically distend the wound bed 1013 into enclosed space 1017 and to release wound bed to a baseline state upon reduction or release of suction.

Wound interface 1015 may be sufficiently deformation resistant to accommodate distention of at least a portion of the wound bed into the enclosed space 1017 when the pressure $p_0$ within the enclosed space is sufficiently below ambient pressure $p_{amb}$. For example, in this implementation, wound interface 1015 maintains concavity 1025 of enclosed space 1017 oriented toward wound bed 1013 at pressures $p_0 < p_{amb}$ to allow for distention of at least portions of the wound bed 1013 into enclosed space 1017.

Figure 3:
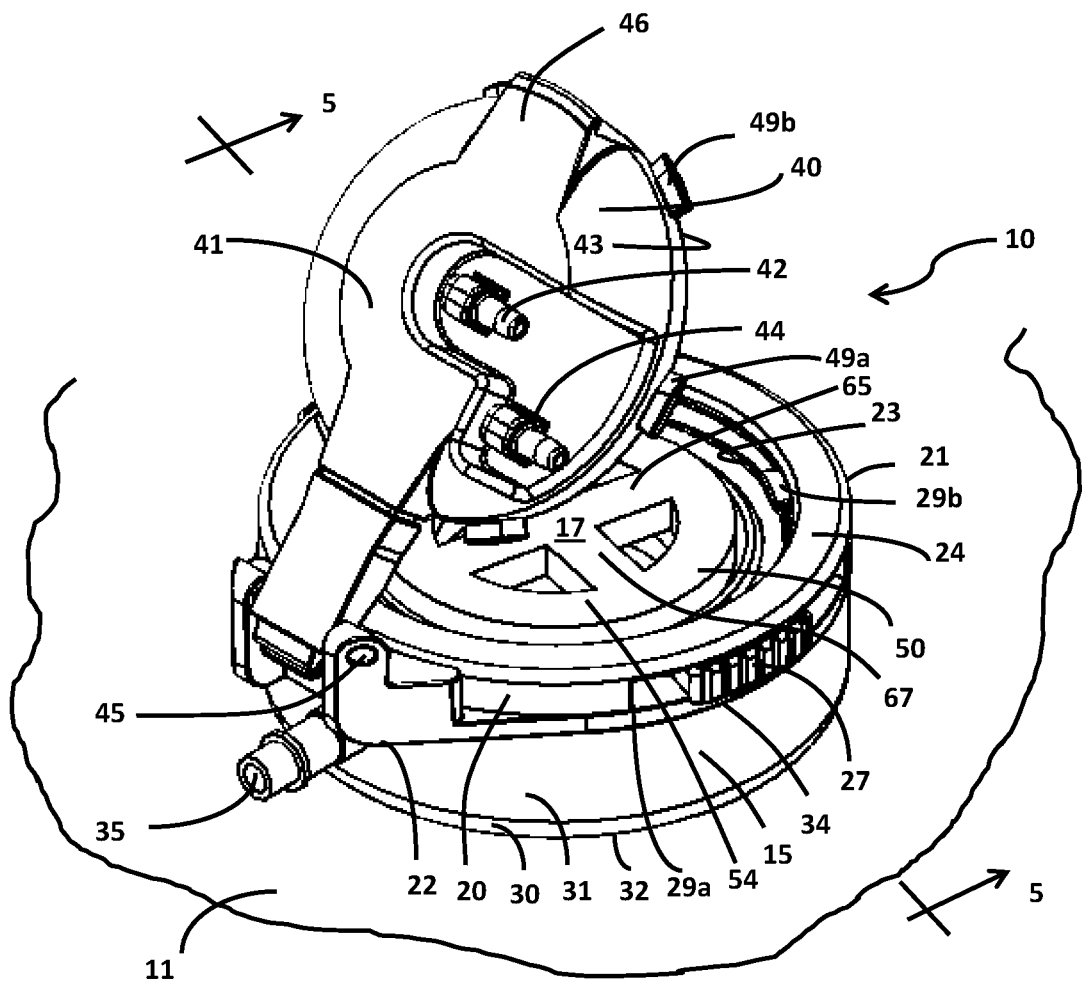
FIG. 3 illustrates by perspective view a second exemplary implementation of a wound therapy apparatus.

FIGS. 3, 4A, 4B, 5A, and 5B illustrated exemplary wound therapy apparatus 10. As illustrated in FIG. 3, exemplary wound therapy apparatus 10 includes wound interface 15, and wound interface 15 includes base 20, cushion 30, and cover 40, with cushion 30 secured circumferentially about the perimeter of base 20 to enclose the perimeter of base 20, and cover 40 secured hingedly to base 20. Base 20, as illustrated, has an annular shape, and base 20 defines outer surface 21 and inner surface 23.

Cushion 30 is annular shaped with footprint corresponding to that of base 20 (see FIG. 5A), and cushion 30 defines outer surface 31 and inner surface 33, as illustrated. Distal surface 32 of cushion 30 (surface of cushion 30 oriented toward patient) is secured circumferentially sealingly to the skin surface 11 via adhesive layer 90, as illustrated, and proximal surface 34 of cushion 30 (surface of cushion 30 oriented toward physician) is secured sealingly to distal surface 22 of base 20 around the circumference of base 20. Cushion 30 cushions the wound interface 15 against the skin surface 11, and sealingly conforms to a contour of the skin surface, in this implementation. Outer surface 21 is generally aligned with outer surface 31, in this implementation, around the entire perimeter of base 20 and cushion 30.

Figure 5A:
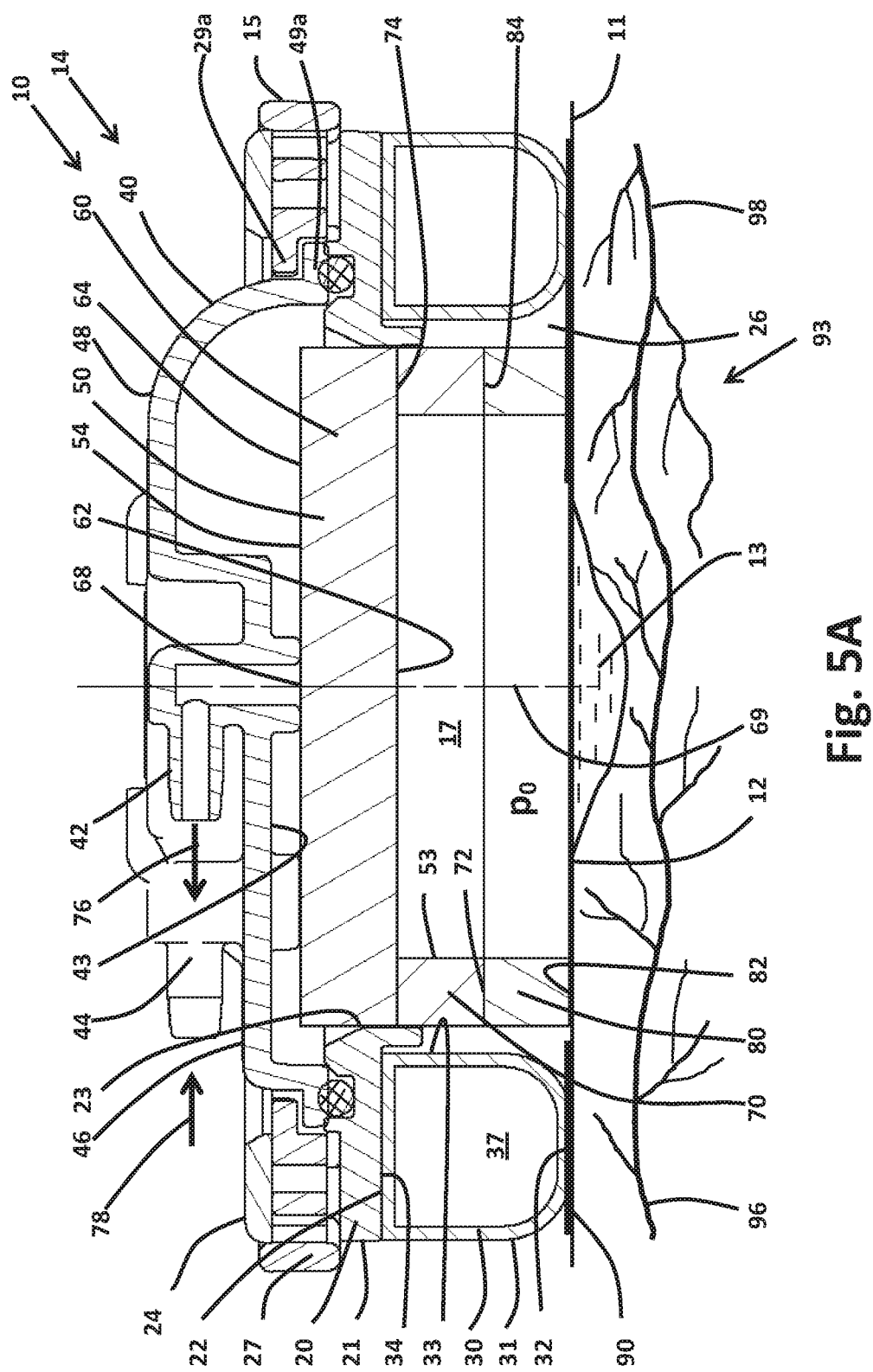
FIG. 5A illustrates by cross-sectional view portions of the exemplary wound therapy apparatus of FIG. 3 at an exemplary first stage of operation.
Figure 5B:
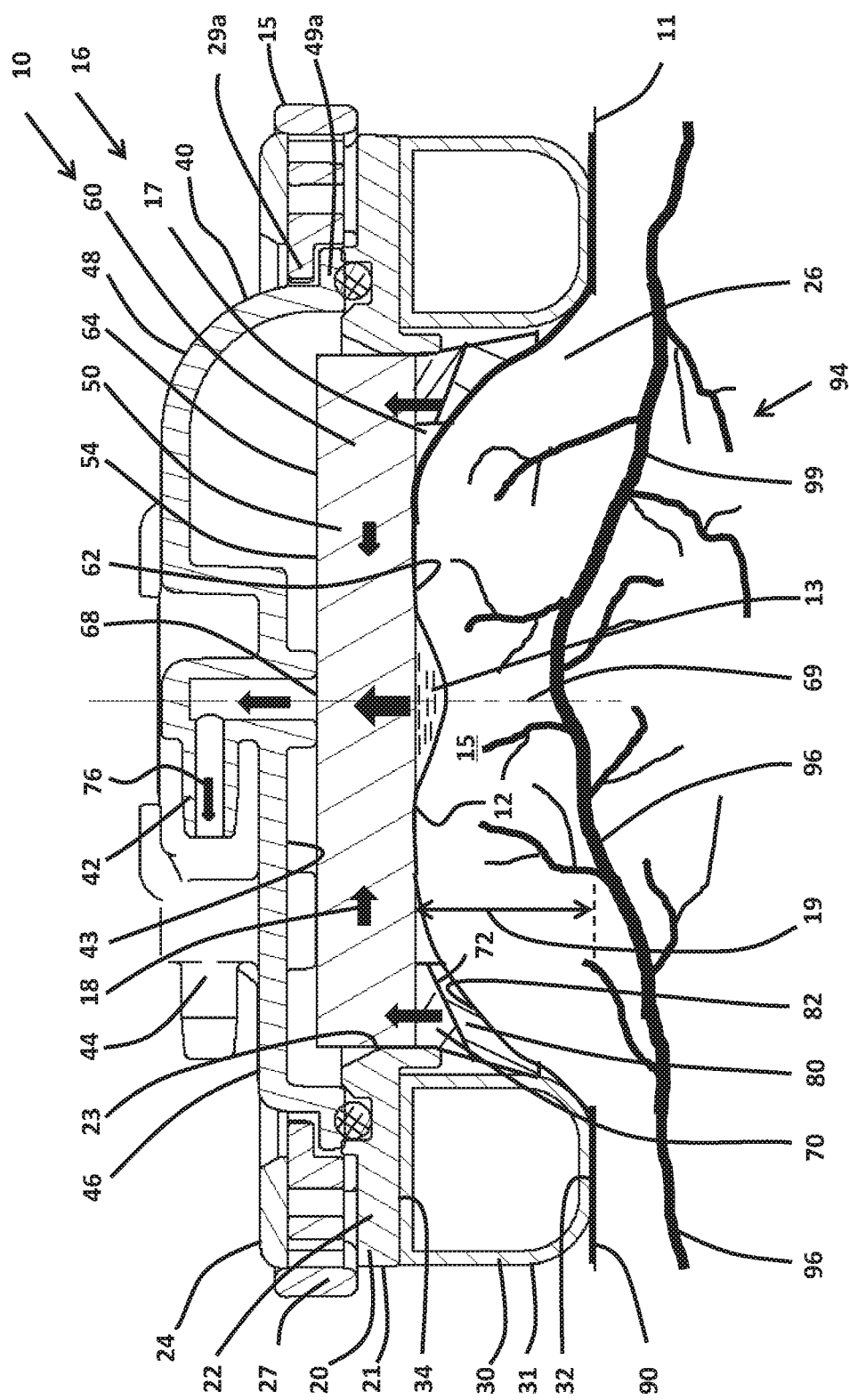
FIG. 5B illustrates by cross-sectional view portions of the exemplary wound therapy apparatus of FIG. 3 at an exemplary second stage of operation.

Cover 40 is hingedly attached to base 20 by hinge 45 that allows cover 40 to be positionable between open position 46, illustrated in FIG. 3, and closed position 48, illustrated in FIGS. 5A and 5B, to disengage or to engage sealingly, respectively, cover 40 with proximal surface 24 of base 20. Hinge 45 may be configured to releaseably engage cover 40 with base 20 to allow cover 40 to be replaced with, for example, a fresh cover, a non-see-through cover, or to a cover with differing functionality such as cover 140 of wound therapy apparatus 100 (see FIGS. 6, 7A, 7B). Hinge 45 may be, for example, a living hinge, pinned hinge, a snap-fit disengageable coupling, or other hinge, as would be understood by one of ordinary skill in the art upon study of this disclosure.

Cover 40 may be engaged with base 20 by various other mechanisms such as a threaded engagement, or frictional engagement, in other implementations, that allow cover 40 to be sealingly engaged with base 20 and allow cover 40 to be disengaged from base 20. Cover 40 may be removably or nonremovably engaged with base 20, in various implementations. Various seals, compression fittings, and so forth may be provided about cover 40, base 20, or cover 40 and base 20 to sealingly engage cover 40 with base 20. Note that hinge 45 is optional, and may be omitted in certain implementations, for example, when no direct intervention to the wound bed 13 is contemplated, as in, for example, exemplary wound therapy apparatus 100 illustrated in FIGS. 6, 7A, and 7B.

With cover in open position 46, various direct interventions into enclosed space 17, for example, debridement of necrotic tissue using medical maggots, placement of a skin or other tissue graft over the wound bed 13, are allowed. With cover 40 in closed position 48 and distal surface 32 of cushion 30 secured circumferentially and sealingly to the skin surface 11, an enclosed space 17 may be defined by inner surface 43 of cover 40, inner surface 23 of base 20, and inner surface 33 of cushion 30, in this implementation, and enclosed space 17 is essentially fluid-tight when wound interface 15 is secured to skin surface 11.

While wound interface 15 is illustrated as cylindrical in shape enclosing a circular region of skin surface 11, it should be understood the wound interface, such as wound interface 15, may assume other geometric shapes such as rectangular, polygonal, or ovoid, to enclose various shaped wounds or regions over skin surface 11, in various other implementations. For example, the wound interface may be ovoid shaped and low profile to enclose a linear incision such as from a Caesarian section. The wound interface may be ovoid and higher profile to enclose the breasts following breast augmentation, or reconstructive breast surgery following mastectomy. The term "annular" as used in this disclosure is intended to include other geometric shapes, such as, for example, polygonal, rectangular, or ovoid, with a circumference surrounding a cavity.

Port 42 and second port 44 are disposed about cover 40, as illustrated, to fluidly communicate with enclosed space 17 between outer surface 41 and inner surface 43 in order that enclosed space 17 may be in fluid communication via port 42 and second port 44 with, for example, fluid reservoir(s), fluid sources, fluid sinks, pump(s), controls, a control module such as control module 880 (see FIG. 14), and sensors external to outer surface 41 via tubing including hoses, pipes, valves, and various other fluid conveyances and fittings that may cooperate with port 42 and second port 44. Port 42 and second port 44 may fluidly communicate with, for example, a compressed mechanical elastomeric bulb, a re-expanding enclosed space that is powered by various spring-like mechanisms, a mechanical or electrical pump, or a pump in combination with additional elements such as one or more sensors, valves, control module, electronic circuitry, tubing, processor and software that may cooperate to deliver fluids and therapies to the enclosed space 17 or withdraw fluids from enclosed space 17. Port 42 is centrally located and second port 44 is located peripherally, in this implementation, but port 42 and second port 44 may be variously located about wound interface 15, with reciprocal or varied flow directions in various other implementations. Input fluid 78 may be input into enclosed space 17 via port 44, and output fluid 76, which may include exudate 18 (see FIGS. 5A & 5B), may be withdrawn from enclosed space 17 via port 42 (see FIGS. 5A and 5B) or with fluid flow in reverse direction.

As illustrated in FIG. 3, detents, such as detents 49a, 49b disposed circumferentially around a perimeter of cover 40 mechanically cooperate with corresponding base detents, 29a, 29b, disposed circumferentially around a rotatable locking ring 27 to releasably retain cover 40 in closed position 48 against base 20 so that enclosed space 17 is fluid-tight. Locking ring 27 is disposed beneath the surface 21 of base 20, as illustrated, and locks or releases cover by rotation or sliding in certain directions, in this implementation.

Various numbers of inter-engaging detents between the cover and base 20 such as detents 49a, 49b and base detents 29a, 29b, and their functional equivalents may be provided in various implementations, and may have various shapes, sizes, mechanisms of operation, and so forth, as would be readily understood by those of ordinary skill in the art upon study of this disclosure. In various implementations, face seals, radial seals, compression seals, with and without O-ring or gaskets, and other seals may be employed to form a fluid tight seal between the cover and base, as would be readily understood by those of ordinary skill in the art upon study of this disclosure.

Cushion 30, in this implementation, defines cushion chamber 37 (see FIGS. 5A & 5B). Cushion 30 is formed, for example, of rubber or a polymer such as PVC or silicone. An optional cushion port 35 extends forth from outer surface 31 of cushion 30 for fluid communication with cushion chamber 37 through cushion port 35. Fluid, including air or other gasses or liquids, within cushion chamber 37 of cushion 30 may be regulated via cushion port 35 to provide the desired level of cushioning and sealing of wound interface 15 with respect to skin surface 11. In other implementations, cushion 30 may be formed, for example, of various compressible, conformable, fluid-impervious closed cell foams.

In various implementations, base 20 may be formed, for example, of one or more medical polymers including, for example, ABS, polystyrene or polypropylene. Cover 40 may be transparent, at least in part, to allow visual inspection of enclosed space 17 including wound bed 13 and portions of skin surface 11 enclosed within enclosed space 17. Cover 40 may be formed, for example, from polycarbonate, acrylic or other clear polymer material such as copolyester available as Eastman Tritan™ available from Eastman Chemical Co.

FIG. 3 illustrates pad 50 disposed within enclosed space 17 of wound therapy apparatus 10. Pad 50, in this implementation, is cylindrical in shape and generally annular to leave portions of enclosed space 17, particularly the space just above the wound bed, unoccupied by pad 50 at least during a certain phase of the therapy such that pad 50 is not in continuous contact with wound bed. Outer surface 51 of pad 50 may be biased against at least portions of inner surface 33 of cushion 30, at least portions of inner surface 23 of base 20, or at least portions of inner surface 43 of cover 40 with cover 40 in closed position 48, in this implementation. In some implementations, pad 50 may be used during the initial exudative phase of wound therapy and is removably received within enclosed space 17 to allow periodic removal and replacement of pad 50 when cover 40 is in open position 46. In other implementations, pad 50 is secured fixedly to wound interface 15 within enclosed space 17, in which case replacement of pad 50 includes replacement of both pad 50 and at least the portions of wound interface 15, such as a detachable and replaceable cover 40, to which pad 50 is fixedly secured.

Figure 4A:
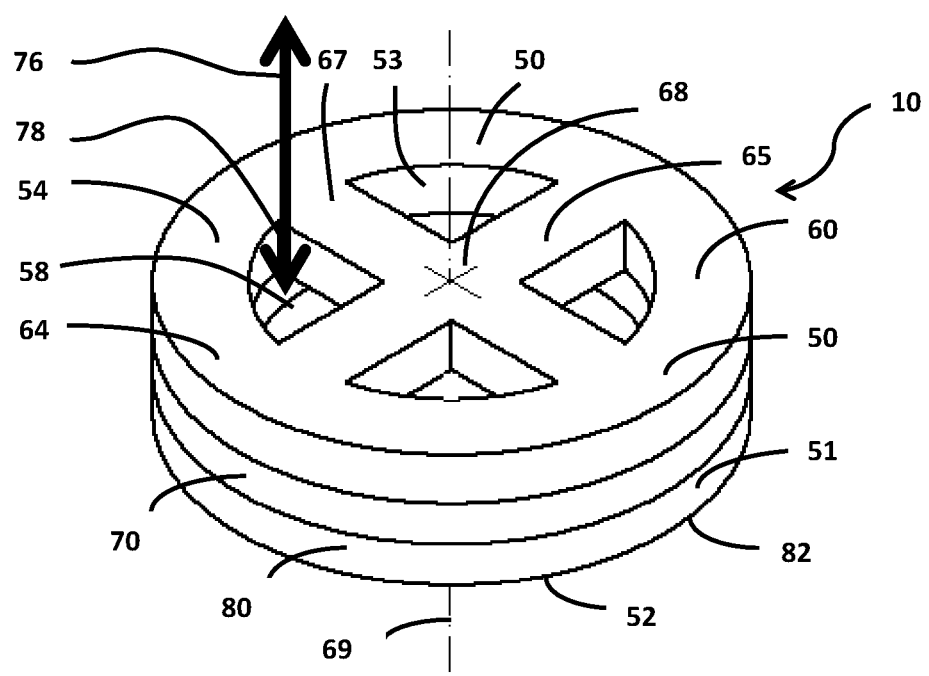
FIG. 4A illustrates by perspective view portions of the exemplary wound therapy apparatus of FIG. 3.
Figure 4B:
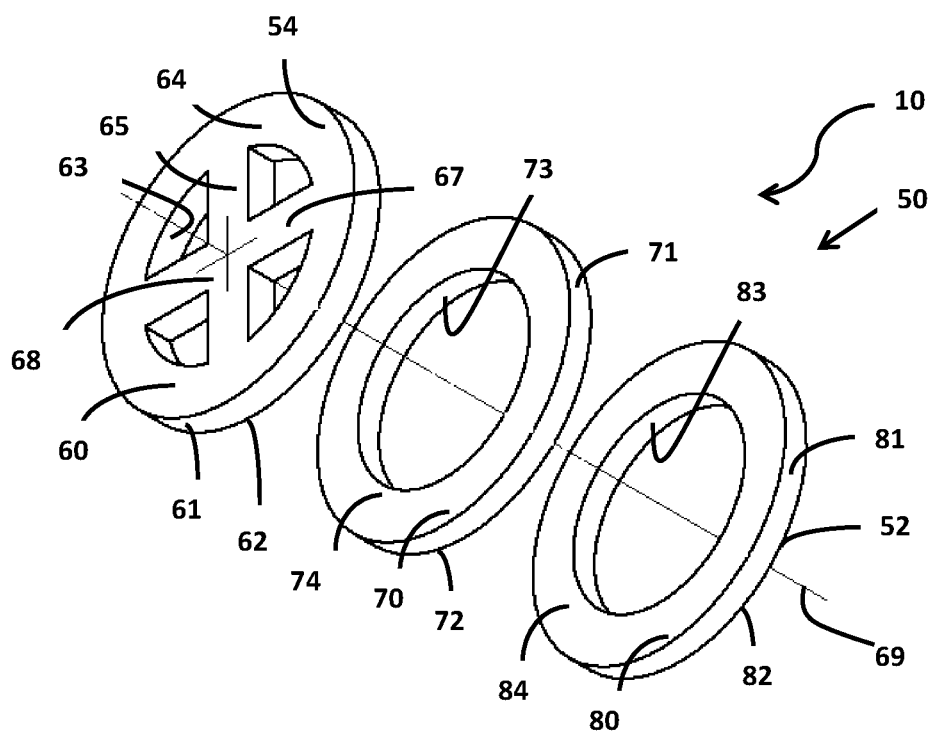
FIG. 4B illustrates by exploded perspective view portions of the exemplary wound therapy apparatus of FIG. 3.

FIGS. 4A and 4B illustrate pad 50 of wound therapy apparatus 10. In this implementation, pad 50 is formed of pad components 60, 70, 80 that are die-cut slices of stock thickness of, for example, absorbent foam. Pad components 60, 70, 80 stackably received with one another may be stitched together or focally glued together in a manner that does not impeded fluid flow through pad 50. When stackably received with one another, distal surfaces 62, 72 are biased against proximal surfaces 74, 84, respectively, as illustrated. When stackably received with one another, proximal surface 64 of pad component 60 forms proximal surface 54 of pad 50, distal surface 82 of pad component 80 forms distal surface 52 of pad 50, inner surfaces 63, 73, 83 form inner surface 53 of pad 50, and outer surfaces 61, 71, 81 form outer surface 51 of pad 50, in this implementation.

Pad 50 may include various numbers of pad components, such as pad components 60, 70, 80, and the number of pad components, such as pad components 60, 70, 80, that form pad 50 may be chosen to result in a selected desired thickness of pad 50. An optional loop of polymer thread may be provided about pad 50 for removal of pad 50 from enclosed space 17. Alternatively, pad 50 may be formed as a unitary structure of preselected dimensions. In various implementations, pad 50 absorbs exudate and functions as a conduit for passage of exudate 18 out of enclosed space 17 via port 42 (FIG. 5B). Pad components 60, 70, 80, in various implementations, may be formed either of the same material or from different materials in different spatial relationships, such as layers or columns, to form differential fluid flow paths or wicking characteristics, if desired. Pad component 60, in various implementations, may have at least one diagonal, instead of a cross-member, such as cross-member 65, 67, or pad component 60 may have three or more cross-members instead of the two cross-members in the illustrated implementation. In some implementations, pad component 60 may be formed as a continuous structure from outer surface 51 to axis 69, in which case the annular region within pad component 60 is omitted. Various implementations of pad 50 may include a single unitary molded or woven structure of selected dimensions.

Pad components 70, 80 are annular in configuration, in the FIG. 4B implementation. Pad component 60 is annular and includes at least one cross member, such as cross-member 65, 67, that emanates from inner surface 63 of pad component 60 and passes through axis 69 of the annulus, as illustrated. Cross-members 65, 67 intersect one another proximate axis 69 to form central portion 68, that communicates fluidly with port 42, which is correspondingly positioned on cover 40 to fluidly communicate with central portion 68 of pad 50 when cover 40 is in closed position 48.

While various designs of absorptive pad 50 may be feasible for exudate withdrawal out of enclosed space 17, peripheral portions of pad 50 lead towards that central portion 68 of pad 50 that contacts port 42 in the illustrated implementation. Exudate 18 may be transmitted through pad 50 to central portion 68 and then be withdrawn from pad 50 through port 42. As illustrated in FIG. 4A, output fluid 76 and input fluid 78 may pass, at least in part, through aperture 58 of pad 50, to communicate with enclosed space 17 or wound bed 13.

FIGS. 5A and 5B further illustrate cross-section views of wound therapy apparatus 10 along axis 5-5 of FIG. 3, with FIG. 5A illustrating wound therapy apparatus 10 at an exemplary first stage of operation 14 and FIG. 5B illustrating wound therapy apparatus 10 at an exemplary second stage of operation 16. Wound interface 15 is sealingly secured to the skin surface 11 to enclose wound boundary 12 such that portions of wound bed 13 at skin surface 11 are enclosed by enclosed space 17, which is fluid-tight, as illustrated in FIGS. 5A and 5B. At least portions of wound bed 13 disposed below skin surface 11 such as undermining, sinus tracts, and tunnels (see FIG. 1) may be in fluid communication with enclosed space 17. Note that it may be possible for wound boundary 12 to be enclosed within enclosed space 17 while undermined areas may extend beneath the skin surface 11 beyond enclosed space 17.

Adhesive layer 90 secures distal surface 32 of cushion 30 to the skin surface 11, as illustrated on the left side of FIG. 5A, and adhesive layer 90 is interposed between distal surface 32 of cushion 30 and skin surface 11. Adhesive layer 90 may optionally extend over portions of skin surface 11 to include all skin surface under and proximate to the footprint of wound interface 15, as illustrated on the right side of FIG. 5A. When adhesive 90 is a medically suitable member of the cyanoacrylate class, such as N-butyl-2-cyanoacrylate (Histoacryl Blue), or octyl-2-cyanoacrylate (Dermabond), the layer of water-resistant adhesive coating over the periwound skin surface function to protect normal skin from maceration, secondary to prolonged exposure to liquids. Adhesive 90 may be, for example, acrylic, silicone or hydrocolloid. Other securement mechanisms such as straps with hook-and-loop-type fasteners may also be employed in various other implementations to secure, at least in part, wound interface 15 to the skin surface 11.

Dressing may be omitted from wound bed 13, so that no dressing is in contact with the wound bed 13 for much of the duration of wound therapy, which allows for direct assessment of the wound condition through transparent portions of cover 40, in various implementations. In certain implementations, pad 50 may be in intermittent contact with the wound bed 13 during certain stages of operation. Even in such implementations, at least a portion of the wound bed may be visible either directly through transparent portions of cover 40 and corresponding apertures 58 in pad 50. The absence of the dressing in constant contact with the wound bed 13 may avoid the problem of painful tearing of granulation tissue during dressing change with concomitant interruption of the healing process. The wound interface 15 may need changing only once a week, resulting in savings of healthcare provider time. In addition, because no dressing is in the wound bed, except perhaps intermittently in the initial exudative phase of wound bed 13, the wound therapy apparatus 10 may be employed from initial treatment until complete healing of the wound bed 13 is achieved. The wound therapy apparatus 10 may support a wide range of therapies, for example, proteolytic enzyme soaks, medical maggot debridement, antibiotic lavage and incubation of tissue stroma, skin grafts, and stem cells, etc.

At first stage of operation 14, illustrated in FIG. 5A, the pressure $p_0 \approx p_{amb}$ within enclosed space 17 of wound therapy apparatus 10. (Note that pressure $p_0 > p_{amb}$ at first stage of operation 14 in some implementations) Wound bed 13 and skin surface 11 within enclosed space 17 are in a baseline state 93 with wound bed 13 in spaced relation with distal side 62 of pad component 60 of pad 50, as illustrated in FIG. 5A, so that wound bed 13 does not directly contact pad 50 particularly distal side 62 of pad component 60. As illustrated in FIG. 5A, wound interface 15 defines entry 26 to enclosed space 17, as illustrated, and the portions of wound bed 13 enclosed within wound interface 15 may generally lie outside (e.g. are not drawn upwards through) entry 26 in baseline state 93. Capillary 96, which is proximate wound bed 13, is in a baseline undilated state 98 and conveys a baseline quantity of blood to wound bed 13, as illustrated.

At second stage of operation 16 of wound therapy apparatus 10, as illustrated in FIG. 5B, pressure $p_0 = p_{min}$ with $p_{min} < p_{amb}$ within enclosed space 17 due to withdrawal of output fluid 76, which may include air and other gasses and liquids as well as exudate 18, from enclosed space 17 through port 42. Pressure $p_0 = p_{min}$ within enclosed space 17 distends at least portions of the wound bed 13 through entry 26 into the enclosed space 17 so that wound bed 13 is in distended state 94, as illustrated in FIG. 5B. In distended state 94, wound bed 13 at skin surface 11 and portions of skin surface 11 enclosed by enclosed space 17 are engorged, distended and stretched, capillary blood vessels 96, including capillaries, arterioles and venules proximate the wound bed, such as capillary 96, may be in a dilated state 99. In dilated state 99, capillaries may be engorged and blood flow about the wound bed 13 may be increased above baseline, with associated salutary benefits. Further, distention including deformation and stretching of tissues surrounding the wound bed has been found to stimulate fibroblast differentiation and wound healing (cf. Saxena, V. et. al., *Vacuum Assisted Closure: Microdeformation of Wound and Cell Proliferation*. Amer. Soc. Plastic Surg. 1086-1096, October 2004).

In distended state 94, portions of wound bed 13, skin surface 11, or portions of wound bed 13 and skin surface 11 may bias against at least portions of pad 50, such as against portions of distal surface 62 of pad component 60, as illustrated in FIG. 5B. In distended state 94, portions of wound bed 13, skin surface 11, or portions of wound bed 13 and skin surface 11 may bias against inner surface 53 of pad 50. Pressure $p_{min}$ may be selected to cause distended state 94 with biased engagement between pad 50 and at least portions of wound bed 13. Pad 50 absorbs exudate 18 (indicated by the solid black arrows in FIG. 5B) from wound bed 13 by biased engagement between pad 50 and wound bed 13. Pad component 80 of pad 50 that surrounds wound bed 13 and contacts skin surface 11, as illustrated, may absorb exudate 18 from peri-wound areas within enclosed space 17. Therefore, in various orientations of wound interface 15, exudate 18 may be absorbed by at least portions of pad 50 and then evacuated from pad 50 by suction through port 42. Following absorption by pad 50, exudate 18 may be transmitted through pad 50 by a combination of capillary action and suction gradient to central portion 68, and the exudate 18 is then withdrawn from pad 50 at central portion 68 through port 42, which is in biased engagement with central portion 68, thereby withdrawing the exudate 18 from enclosed space 17. When suction is relieved by input of input fluid 78 via a second port 44, the input of input fluid 78 into the enclosed space, particularly if it is abrupt, may provide a propulsive force forward to propel exudate 18 in pad 50 and beyond in tubing connected to port 42 into a canister, such as canister 881 (see FIG. 14) to unclog the tubing. Note that output fluid 76 withdrawn from enclosed space 17 may include gaseous fluids or other liquids within enclosed space 17 along with exudate 18 in order to decrease pressure $p_0$ within enclosed space 17.

Wound therapy apparatus 10 may be varied periodically between first stage of operation 14 and second stage of operation 16 by varying pressure $p_0$ within enclosed space 17 periodically generally over the pressure range $p_{min} \leq p_0 \leq p_{amb}$ where $p_{min}$ is the minimum pressure over a periodic pressure variation. Pressure $p_0$ may be varied by input of input fluid 78 into enclosed space 17 and withdrawal of output fluid 76 from enclosed space 17, and a control module, such as control module 880 of wound therapy apparatus 800 (see FIG. 14) may be operably connected to wound interface 15 to input the input fluid 78 into enclosed space 17 and to withdraw output fluid 76 from enclosed space 17. The minimum pressure may be, for example, $p_{min} \approx p_{amb} - 150$ mm Hg. The minimum pressure may be, for example, $p_{min} \approx p_{amb} - 70$ mm Hg. The minimum pressure may be, for example, generally within the pressure range $(p_{amb} - 130 \text{ mm Hg}) \leq p_{min} < (p_{amb} - 80 \text{ mm Hg})$. The minimum pressure $p_{min}$ may be generally within the pressure range $(p_{amb} - 90 \text{ mm Hg}) \leq p_{min} < p_{amb}$.

In various implementations, the periodic variation of the pressure $p_0$ may be generally within the pressure range $p_{min} \leq p_0 \leq p_{max}$ where $p_{max} > p_{amb}$. For example, $p_{max} \approx (p_{amb} + 30 \text{ mm Hg})$. In some implementations, $p_{max} \approx p_{amb}$. In yet other implementations, $p_{max} < p_{amb}$, for example, the maximum pressure $p_{max}$ may range between about −5 mm Hg and about −20 mm Hg below ambient pressure $p_{amb}$, in certain implementations.

As wound therapy apparatus 10 is varied from first stage of operation 14 to second stage of operation 16, the pressure $p_0$ decreases with $p_0 \rightarrow p_{min}$ and wound bed 13 is distended through entry 26 into enclosed space 17 to have distention length 19 in distended state 94 at second stage of operation 16. Wound bed 13 is released from tension into baseline state 93 as pressure $p_0$ increases with $p_0 \rightarrow p_{max}$ as wound therapy apparatus 10 is varied from second stage of operation 16 to first stage of operation 14. Wound bed 13 in baseline state 93 has essentially no distention length, such as distention length 19, at first stage of operation 14. Thus at least portions of the wound bed 13 distend into enclosed space 17 and are released from distention into the enclosed space 17 between distended state 94 and baseline state 93, respectively, periodically in correspondence as the pressure $p_0$ is varied periodically over the pressure range $p_{min} \leq p_0 \leq p_{max}$. Periodic variation of pressure $p_0$ generally over the pressure range $p_{min} \leq p_0 \leq p_{max}$ may massage the wound bed including surrounding tissues to induce corresponding periodic surges of fresh blood flow into the wound bed that provide, for example, nutrients, immune factors and oxygen.

Furthermore, the periodic variation of pressure $p_0$ results in transient, intermittent contact between pad 50 and wound bed 13, in this implementation, so that granulation tissue of wound bed 13 will not have time to grow into pad 50, and, in turn, will not become torn or disrupted when pad 50 or wound interface 15 including pad 50 is replaced. At a particular time during the pressure variation, the pressure $p_0$ may be generally constant throughout enclosed space 17, so that the entirety of wound bed 13 is exposed to pressure $p_0$, and, thus, no significant pressure gradient is created about wound bed 13 that may, for example, decrease blood flow proximate the wound boundary 12. Note that pad 50 may become distended due to absorbtion of exudate 18 so that pad 50 remains in varying degrees of engagement with wound bed 13 as the pressure $p_0$ is varied periodically over the pressure range $p_{min} \leq p_0 \leq p_{max}$ distending the wound bed to increase contact between wound bed 13 and pad 50 or retracting the wound bed 13 thus decreasing contact between wound bed 13 and pad 50 but with the pad 50 always in contact with wound bed 13.

Input fluid 78 in the form of gas or gaseous mixtures may be introduced into enclosed space 17 via second port 44, to regulate, at least in part, the pressure $p_0$ within enclosed space 17 or to control the composition of the gaseous fluids within enclosed space 17. For example, wound therapy apparatus 10 may be periodically varied between first stage of operation 14 and second stage of operation 16 by introduction of input fluid 78 into enclosed space 17 via second port 44 and evacuation of output fluid 76 from enclosed space 17 via port 42. Input fluid 78 introduced into enclosed space 17 via second port 44 and evacuated from enclosed space 17 through port 42, or vice versa, may enhance the withdrawal of exudate 18 from enclosed space 17, and may prevent clogging by increasing fluid velocities in fluid pathways through increased flow volume. Oxygen supplementation, in some instances, is especially important to rescue hypoxic tissue on the verge of death, and to support cellular function such as cell division and collagen synthesis, and input fluid 78 may include gas with an $O_2$ concentration greater than that of atmospheric air. The added oxygen may inhibit anaerobic bacteria growth. The input fluid 78 may be a liquid, such as saline, to rinse the wound, enclosed space and evacuation tubing, or other therapeutic fluid including antibiotic rinse, or amniotic fluid for its regeneration stimulating effects.

Figure 6:
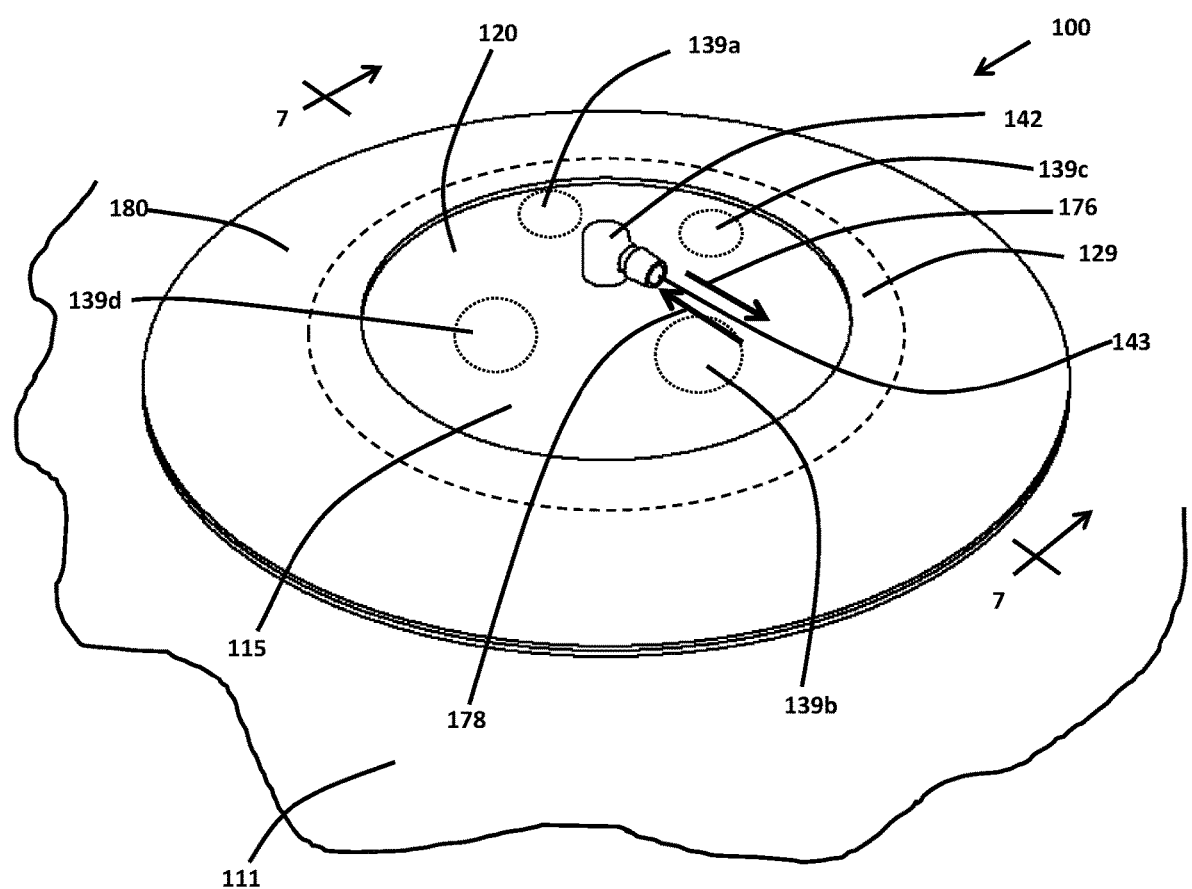
FIG. 6 illustrates by perspective view a third exemplary implementation of a wound therapy apparatus.
Figure 7A:
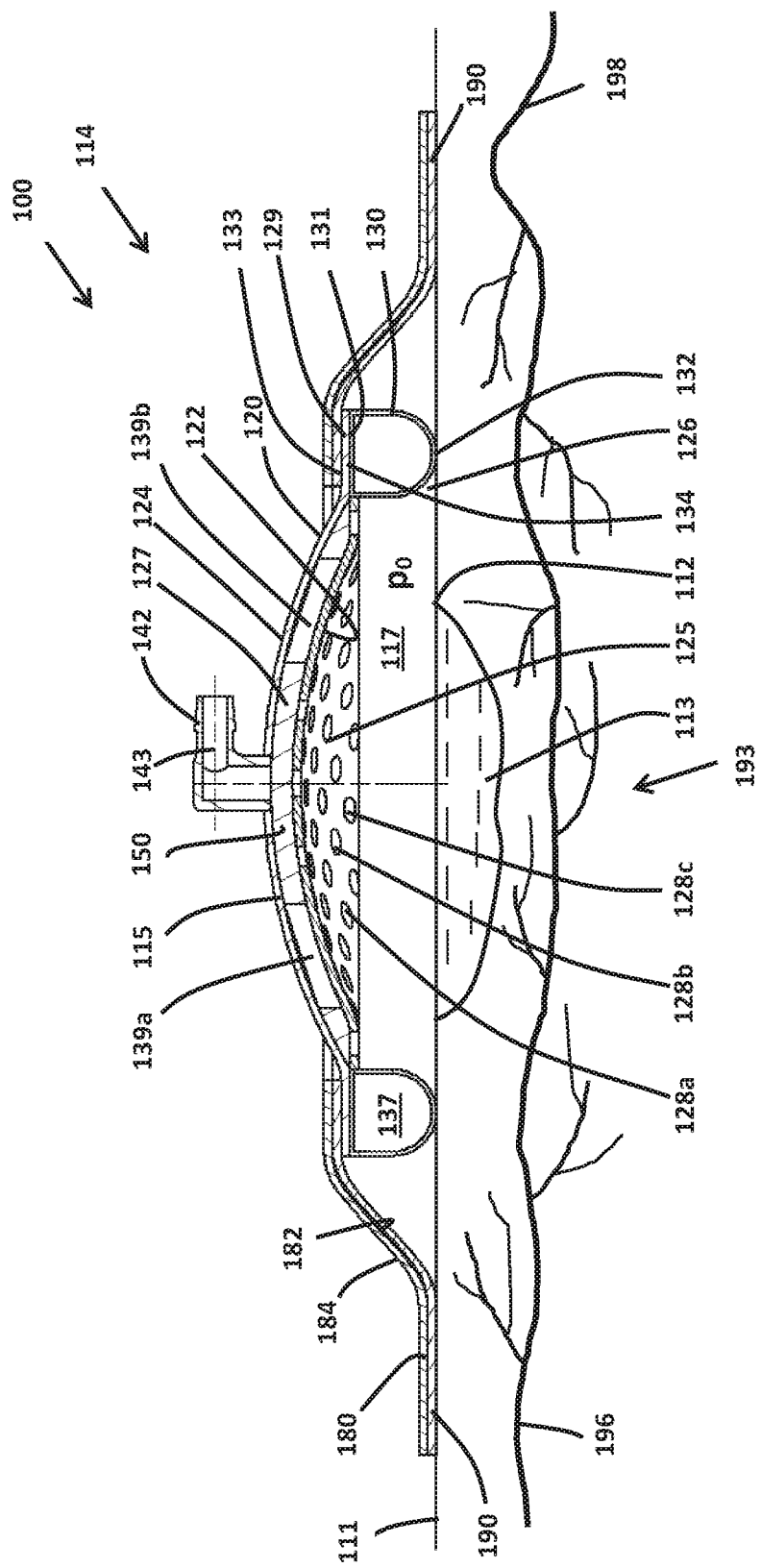
FIG. 7A illustrates by cross-sectional view portions of the exemplary wound therapy apparatus of FIG. 6 at an exemplary first stage of operation.
Figure 7B:
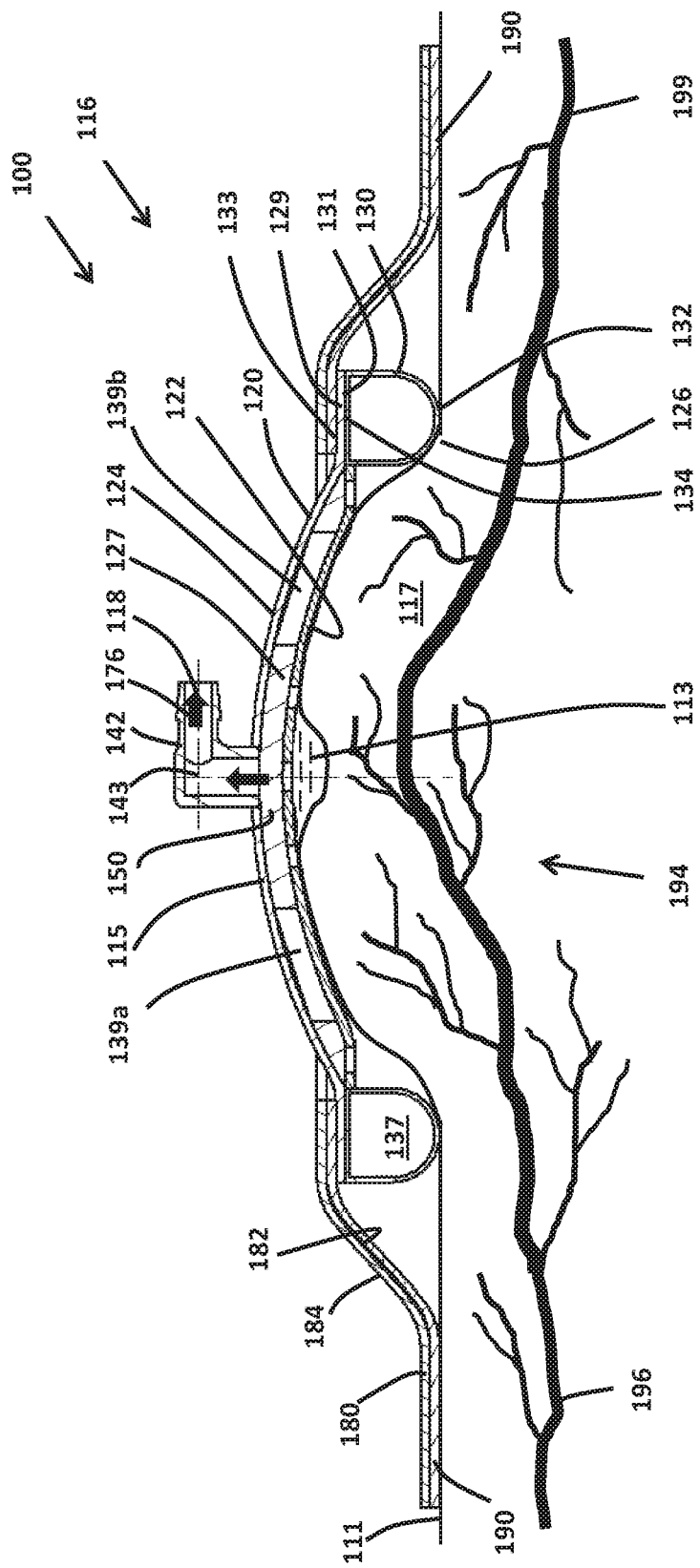
FIG. 7B illustrates by cross-sectional view portions of the exemplary wound therapy apparatus of FIG. 6 at an exemplary second stage of operation.

FIGS. 6, 7A and 7B illustrate another exemplary implementation of a wound therapy apparatus 100. As illustrated in FIG. 6, wound interface 115 of wound therapy apparatus 100 includes base 120, and apron 180. Apron 180 is coated on its underside with adhesive 190, and apron, 180 is annular in shape and disposed about the entire perimeter of base 120 with base 120 occupying portions of the annular region defined by apron 180, in this implementation. A distal perimeter of apron 180 is sealingly secured to skin surface 111 by adhesive 190, in this implementation. Apron 180 may be sized to provide adhesion sufficient to retain wound interface 115 in attachment to the skin surface 111. Apron 180 may be formed of a bandage material such as polyurethane. As illustrated in FIG. 6, wound interface 115 includes port 142 located about wound interface that defines lumen 143 for fluid communication with enclosed space 117. Input fluid 178 may be input or output fluid 176 may be withdrawn from enclosed space 117 via lumen 143 of port 142, as indicated by the arrows in FIG. 6.

As illustrated in FIG. 7A, wound interface 115 of wound therapy apparatus 100 includes cushion 130 and apron 180 secured to flange 129 of base 120. Wound interface 115, in this implementation, is deformation resistant. Flange 129 is secured sealingly about the entirety of the perimeter of base 120, in this implementation, and flange may be pressure-diffusing and conformable to skin surface 111. Flange 129, for example, may be made of a medical polymer such as polyethylene terephthalate (PET), polytetrafluoroethylene (PTFE), polypropylene (PP), polyurethanes (PU), and silicones that may be sealingly secured to skin surface 111 by adhesive. Cushion 130 is optional and may aid in diffusing focal pressure or in providing a fluid-tight seal between wound interface 115 and skin surface 111.

As illustrated in FIG. 7A, cushion 130 has an annular shape and cushion 130 is secured circumferentially around the entire perimeter of base 120. Proximal side 134 of cushion 130 is secured sealingly to distal side 131 of flange 129 around the entire circumference of base 120, as illustrated. Distal side 132 of cushion 130 is biased against skin surface 111 about wound bed 113 to cushion wound therapy apparatus with respect to the skin surface 111 or to conform to the contour of skin surface 111, as illustrated in FIG. 7A. Cushion 130 defines cushion chamber 137, in this implementation. Cushion 130 may be omitted in certain implementations, in which case base 120 may be held in biased engagement with the skin surface 111 by apron 180, by distal side 131 of flange 129, or by both apron 180 and distal side 131 of flange 129 in cooperation with adhesive layer 190. Base 120 may be supported by apron 180 to be in spaced relation with skin surface 111 in implementations that omit cushion 130.

Apron 180 is secured sealingly to proximal side 133 of flange 129, and apron 180 is secured sealingly to the skin surface 111 around the entire perimeter of base 120 by adhesive layer 190 so that wound boundary 112 is enclosed by fluid tight enclosed space 117, as illustrated.

As illustrated in FIG. 7A, portions of base 120 bifurcate to define interstice 127, and pad 150 is received within at least portions of interstice 127. Passages, such as passage 128a, 128b, 128c, are formed in at least portions of distal side 122 of base 120 that allow fluid communication between enclosed space 117 and interstice 127 including pad 150 that is received within interstice 127, in this implementation. Exudate 118 emanating from wound 113 may pass through passages, such as passage 128a, 128b, 128c, into interstice 127 to be absorbed by pad 150. Port 142, as illustrated, fluidly communicates with interstice 127 including pad 150 via lumen 143 to evacuate output fluid 176 including exudate 118 from pad 150. Output fluid 176 may be evacuated from enclosed space 117 through lumen 143 of port 142 as enclosed space 117 fluidly communicates with port 142 through the passages, such as passage 128a, 128b, 128c. Various numbers of passages, such as passage 128a, 128b, 128c, may be provided in various implementations. Port 142, as well as any additional ports may be configured for attachment to tubing for the communication of fluids via tubing with enclosed space 117 through port 142. A control module, such as control module 880 of wound therapy apparatus 800 (see FIG. 14), may be operably connected to lumen 143 of port 143 to input the input fluid 178 into interstice 127 and enclosed space 117 through lumen 143 or withdraw output fluid 176 including exudate 118 from enclosed space 117 and interstice 127 through lumen 143.

Base 120 includes one or more window(s), such as windows 139a, 139b, 139c, 139d, formed of transparent material to allow visual inspection of wound 113 through base 120 and through pad 150, in this implementation. Windows 139a, 139b, 139c, 139d pass between proximal side 124 and distal side 122 of base 120 including portions of interstice 127, as illustrated.

At exemplary first stage of operation 114, as illustrated in FIG. 7A, the pressure $p_0 \approx p_{amb}$ within enclosed space 117. Wound bed 113 is in a baseline state 193, and wound bed 113 is in spaced relation with portions of distal side 122 of base 120 including passages, such as passage 128a, 128b, 128c, so that wound bed 113 does not directly contact the passages or pad 150. As illustrated in FIG. 7A, wound interface 115 defines entry 126 to enclosed space 117, and the portions of wound bed 113 enclosed by enclosed space 117 may generally lie outside entry 126 in baseline state 193.

At exemplary second stage of operation 116 of wound therapy apparatus 100, as illustrated in FIG. 7B, enclosed space 117 is evacuated, in part, by withdrawal of output fluid 176 from enclosed space 117 through lumen 143 of port 142 so that the pressure $p_o$ within enclosed space 117 is less than ambient pressure $p_{amb}$ (i.e., $p_0 < p_{amb}$), which causes at least portions of wound bed 113 to be distended into enclosed space 117 through entry 126 in distended state 194 with at least portions of wound bed 113 biased against distal side 122 of base 120 including passages, such as passage 128a, 128b, 128c. Exudate 118 may thus be withdrawn from wound bed 113 through the passages, such as passage 128a, 128b, 128c, into interstice 127 for adsorption by pad 150 at second stage of operation 116. Pad 150 fluidly communicates with lumen 143 of port 142 so that exudate 118 may be evacuated from pad 150 through port 142 as at least a portion of output fluid 176 via external suction applied to port 142.

Wound therapy apparatus 100 may be varied periodically between first stage of operation 114 and second stage of operation 116 by varying pressure $p_0$ within enclosed space 117 periodically generally over the pressure range $p_{min} \leq p_0 \leq p_{max}$ to distend wound bed 113 into enclosed space 117 in distended state 194 and to release wound bed 113 from distention into enclosed space 117 back to baseline state 193, respectively, thereby massaging wound bed 113. Generally $p_{min} < p_{amb}$ and $p_{amb} \leq p_{max}$, in this implementation. At a particular time during the pressure variation, the pressure $p_0$ may be generally constant throughout enclosed space 117, so that the entirety of wound bed 113 is exposed to pressure $p_0$, that, for example, may result in increased blood flow proximate the wound boundary. Periodically releasing wound bed 113 from contact with distal side 122 of base 120 may prevent wound bed 113 from becoming attached to distal side 122 of base 120, passages, such as passage 128a, 128b, 128c, or pad 150. The wound interface 115 may be sufficiently deformation resistant to maintain fluid tightness of enclosed space 117 when pressure $p_0=p_{min}$, thereby allowing wound bed 113 to be distended into enclosed space 117 and released from distention back to a baseline state 193. The wound interface 115 may be sufficiently deformation resistant to maintain enclosed space 117 with entry 126 when pressure $p_0=p_{min}$, thereby allowing wound bed 113 to be distended into enclosed space 117 and released from distention back to a baseline state 193.

Capillary 196, which is proximate wound bed 113, is in a baseline undilated condition 198 and conveys a baseline quantity of blood to wound bed 113 when wound bed 113 is in baseline state 193 at first stage of operation 114, as illustrated in FIG. 7A. Capillary vessels proximate the wound bed, such as capillary 196, may be in a dilated state 199 when wound bed 113 is in distended state 194 at second stage of operation 116, as illustrated in FIG. 7B.

Input fluid 178 may be input into enclosed space 117 via port 142, as indicated by the arrow in FIG. 6, for example, to regulate, at least in part, the pressure $p_0$ within enclosed space 117, to control the composition of the gaseous fluids within enclosed space 117, or for various therapeutic purposes. For example, wound therapy apparatus 100 may be periodically varied between first stage of operation 114 and second stage of operation 116 by consecutive input of input fluid 178 into enclosed space 117 and withdrawal of output fluid 176 from enclosed space 117 via port 142.

Figure 8:
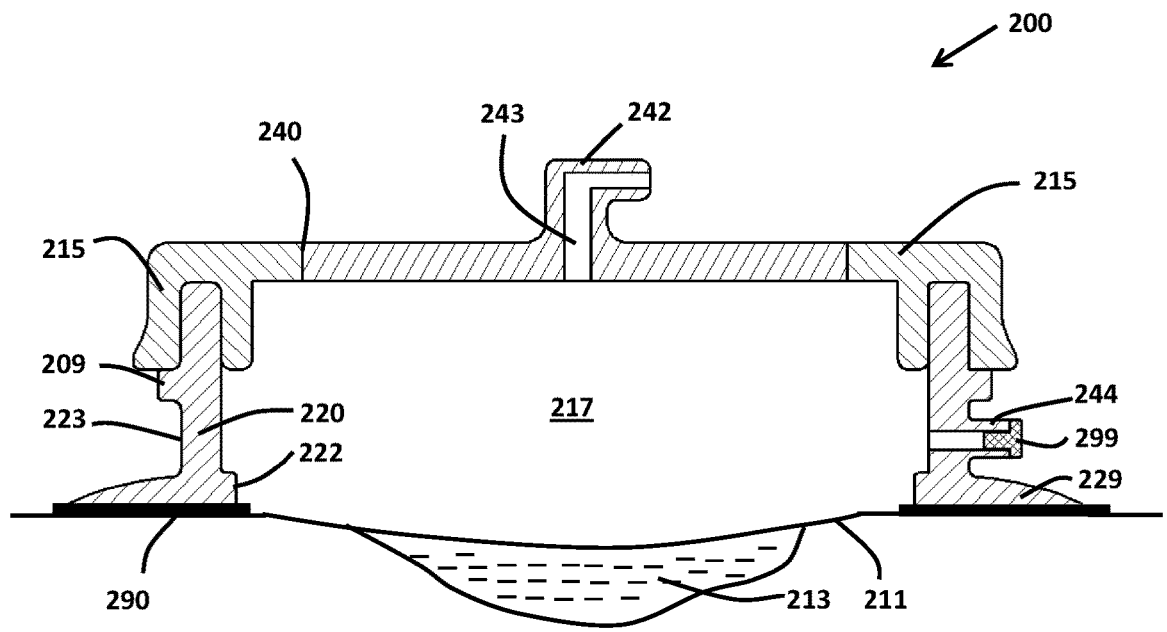
FIG. 8 illustrates by cross-sectional view portions of a fourth exemplary implementation of a wound therapy apparatus.

FIG. 8 illustrates exemplary wound therapy apparatus 200. As illustrated in FIG. 8, wound therapy apparatus 200 includes wound interface 215 that is deformation resistant and defines enclosed space 217 that is fluid-tight when engaged with skin surface 211 to enclose wound bed 213 at skin surface 211. Wound interface 215, as illustrated in FIG. 8, includes cover 240 slidably sealingly frictionally removably engaged with base 220. Cover 240 may include at least transparent portions to allow visual inspection of wound bed 213 though cover 240. Base 220 may include flange 209 around an outer perimeter of base 220 that may provide structural support or sealing surface in cooperation with cover 240, as illustrated. In other implementations, cover 240 and base 220 may be formed as a unitary structure.

Base 220 may include flange 229 around a perimeter of outer side 223 generally at distal end 222 of base 220 with flange 229 secured to skin surface 211 by adhesive 290, as illustrated in FIG. 8. Flange 229 may be designed by thickness and/or polymeric material to be soft and conformable to skin surface 211 to enable sealing of wound interface 215 over a wound 213 in a fluid-tight manner while distributing forces on wound interface 215 from pressure $p_0$ within enclosed space 217 over the skin surface 211. Port 242, which is located about wound interface 215, is in fluid communication with enclosed space 217 via lumen 243. A pad, such as pad 50, 150, 450, 550, 650, 750 (see FIGS. 10, 11A, 11B, 12 and 13A), may be deployed within cavity 217, and the pad may be in fluid communication with lumen 243 of port 242 to allow transfer of exudate from wound bed 213 through the pad and thence through lumen 243 of port 242. One or more additional ports, such as port 244, in communication with enclosed space 217 may be situated about the wound interface 215 for monitoring intra-enclosed space parameters within enclosed space 217, communication of fluids with enclosed space 217, or other therapeutic interventions with enclosed space 217. When not in use, port 244 may be sealed by valve 299 including but not limited to, for example, plugs, clamps, various stopcocks and solenoid valves.

Figure 9:
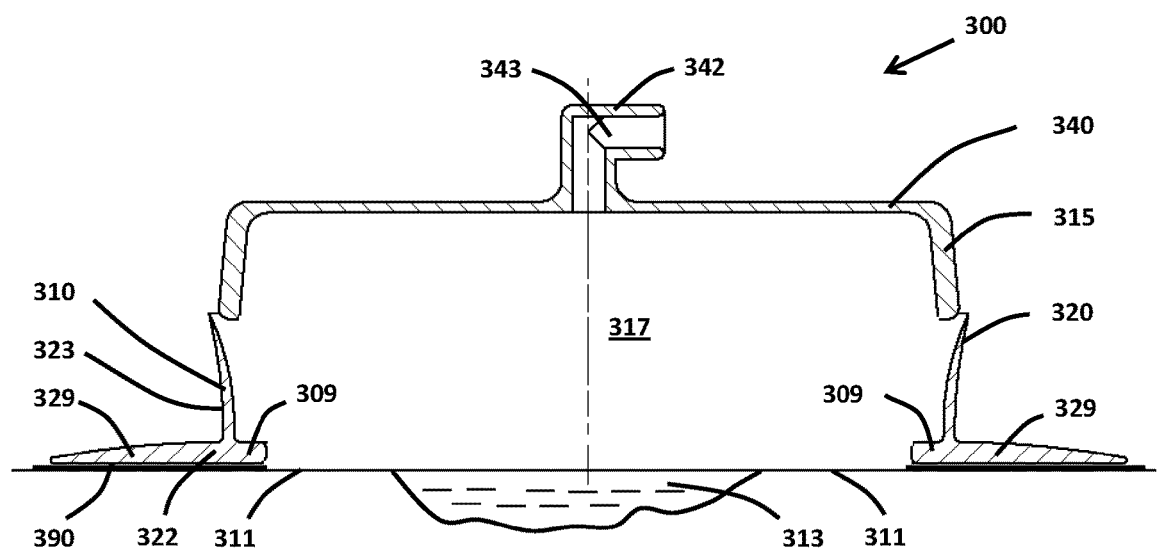
FIG. 9 illustrates by cross-sectional view portions of a fifth exemplary implementation of a wound therapy apparatus.

FIG. 9 illustrates exemplary wound therapy apparatus 300. As illustrated in FIG. 9, wound therapy apparatus 300 includes wound interface 315, and wound interface 315 includes base 320 and cover 340. Base 320 is formed to include flange 329 and receptacle 310. Flange 329 is an annular structure that extends forth from outer side 323 at distal end 322 of base 320. Flange 329 may be formed as a unitary part of base 320. Flange 329 may be adhesively attached to skin 311 around wound bed 313 by adhesive 390, as illustrated in FIG. 9. Cover 340 may be inserted into an aperture defined by receptacle 310, which is fluted to ease insertion, as illustrated in FIG. 9. Stop 309, which forms an inward flange, limits insertion of cover 340 into receptacle 310, and provides additional seal surface between cover and base to form a fluid-tight seal between cover 340 and base 320 so that cavity 317 is fluid-tight, in this implementation. A pad, such as pad 50, 150, 450, 550, 650, 750, may optionally be deployed within cavity 317 in fluid communication with lumen 343 of port 342.

Figure 10:
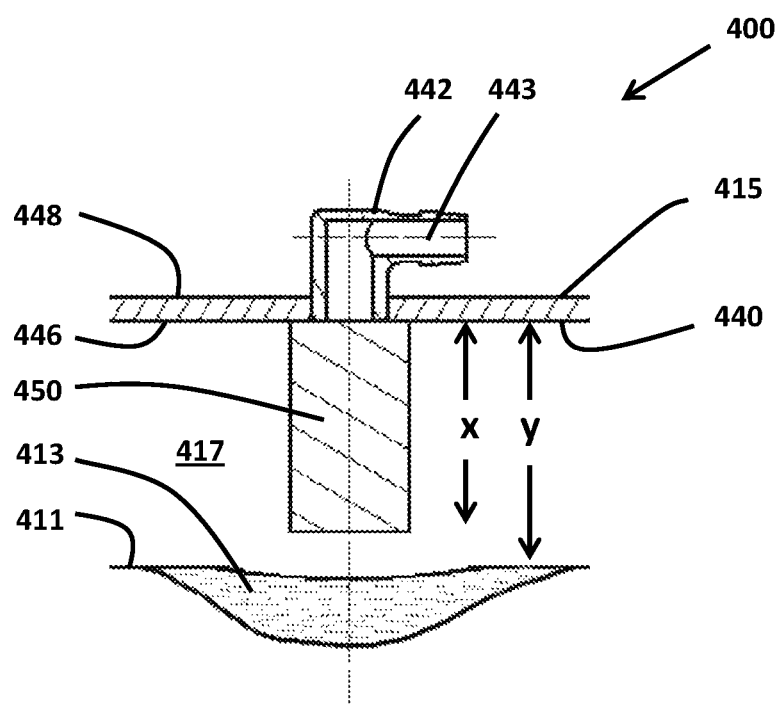
FIG. 10 illustrates by cross-sectional view portions of a sixth exemplary implementation of a wound therapy apparatus.

FIG. 10 illustrates portions of exemplary wound therapy apparatus 400. As illustrated in FIG. 10, wound interface 415 includes cover 440 that defines, in part, enclosed space 417 that encloses wound bed 413 at skin surface 411, and pad 450 is attached to inner surface 446 of cover 440 to communicate with lumen 443 of port 442 and to communicate with at least portions of wound bed 413 when the pressure $p_0$ within enclosed space 417 is reduced thereby causing wound bed 413 to be distended into contact with pad 450. With wound bed 413 in contact with pad 450, exudate may be communicated from wound bed 413 into pad 450 and out of enclosed space 417 via lumen 443 of port 442. Lumen 443 passes between inner surface 446 and outer surface 448 of cover 440, as illustrated.

In this implementation, pad 450 is generally a unitary structure with a columnar configuration that extends forth from distal side 446 of cover 440 to be in contact with the wound bed 413 during at least a portion of a periodic pressure variation. Length X of pad 450 may be less than length Y from distal side 442 of cover 440 to the skin surface 411 or to wound bed 413. Although pad 450, if soft and compressible, may be structured to contact the wound bed 450 at all times (X=Y), one result of X<Y is that pad 450 comes into contact with the wound bed 413 only when pressure $p_0$ within enclosed space 417 is sufficiently below $p_{amb}$ to distend wound bed 413 into contact with pad 450. Exudate withdrawal from wound bed to pad 450 and in turn out of enclosed space 417 through port 442 may occur during such intermittent contact.

Figure 11A:
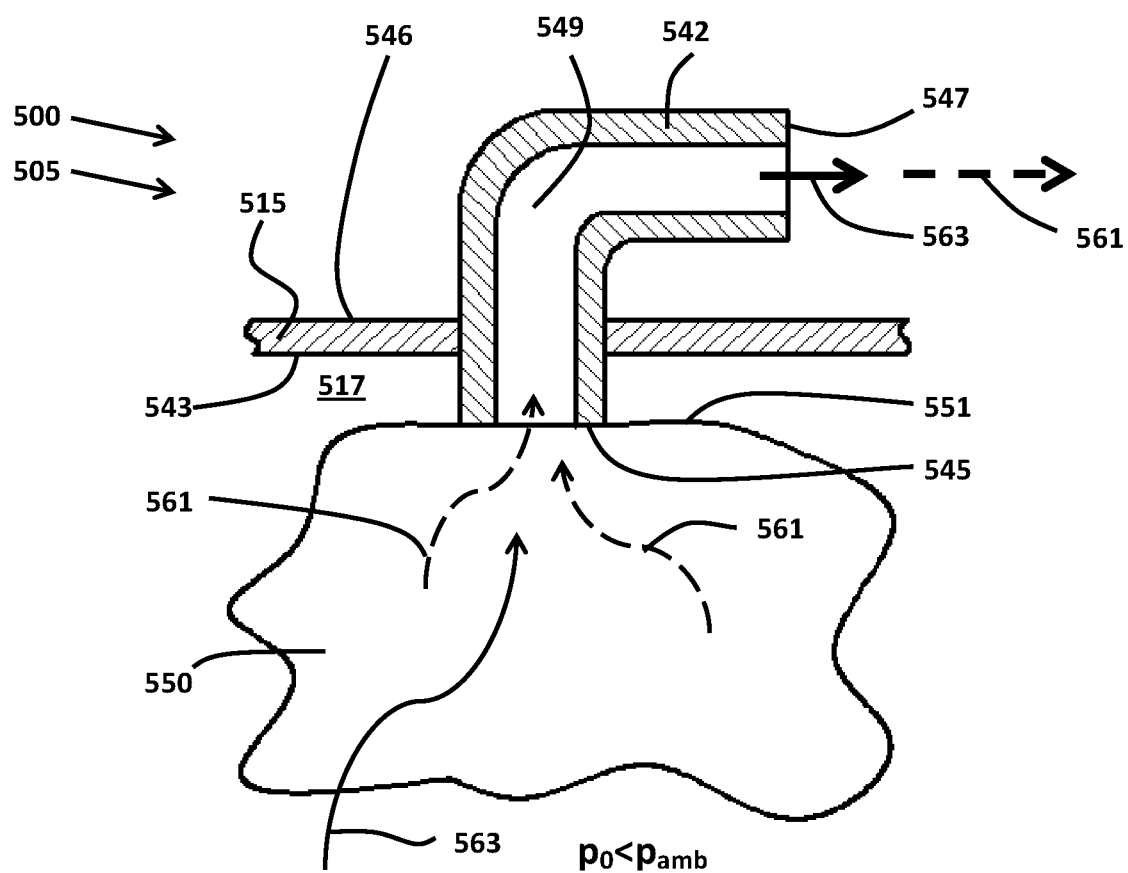
FIG. 11A illustrates by cross-sectional view portions of a seventh exemplary implementation of a wound therapy apparatus in a first stage of operation.
Figure 11B:
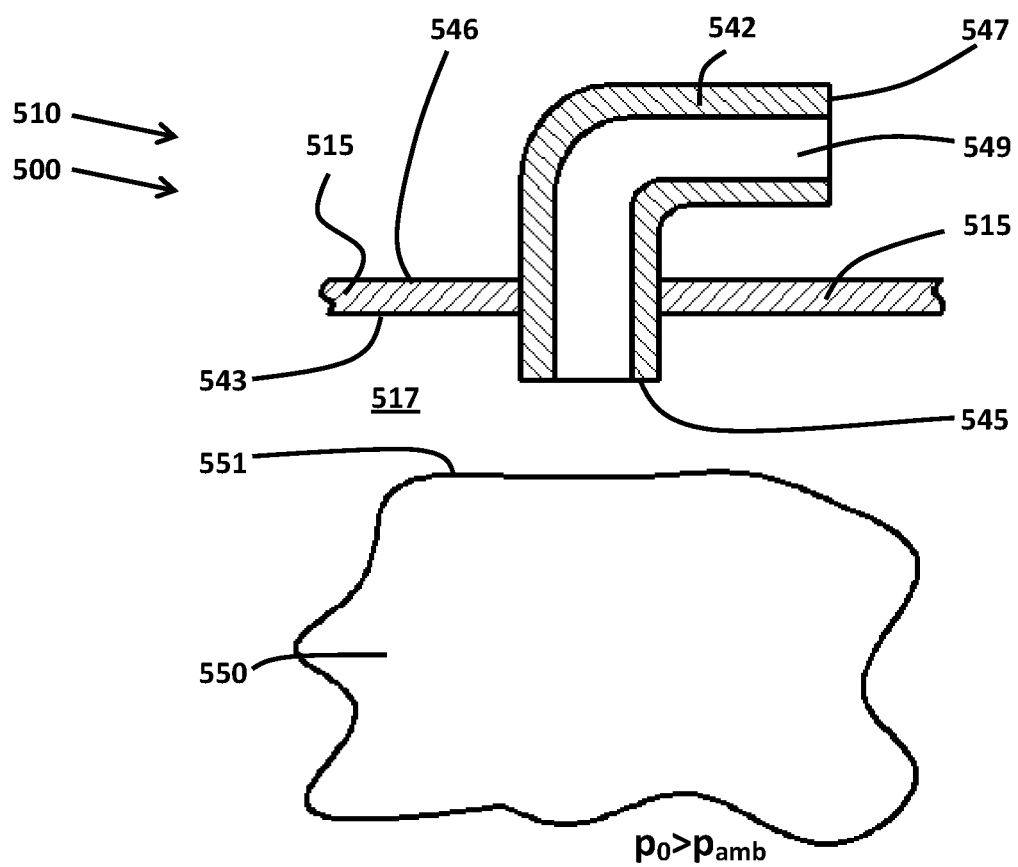
FIG. 11B illustrates by cross-sectional view portions of the exemplary implementation of a wound therapy apparatus of FIG. 11A in a second stage of operation.

FIGS. 11A and 11B illustrate exemplary wound therapy apparatus 500 in exemplary stages of operation 505, 510, respectively. Exemplary wound therapy apparatus 500, as illustrated, includes wound interface 515 with inner surface 543 and outer surface 546 with inner surface 543 defining enclosed space 517. Pad 550 is disposed within enclosed space 517, as illustrated, and port 542 forms lumen 549 between interior end 545 and exterior end 547 of port 542. Lumen 549 passes through wound interface between inner surface 543 and outer surface 546 for fluid communication with enclosed space 517.

As illustrated in FIG. 11A, at first stage of operation 505, the pressure $p_0$ within enclosed space is less than $p_{amb}$. Output fluid 563 in the form of gas is being evacuated from enclosed space 517 through pad 550 and then through lumen 549 from interior end 545 to exterior end 547, as indicated by a solid arrow in FIG. 11A. The resulting pressure gradient causes portions of side 551 of pad 550 to bias against interior end 545 of port 542, as illustrated. Exudate 561, as indicated by dashed arrows in FIG. 11A, is drawn through pad 550 and then through lumen 549 from interior end 545 to exterior end 547. Note that, in various implementations, output fluid 563 may include liquid, gas, or combinations of liquid(s) and gas(ses).

At second stage of operation 510, as illustrated in FIG. 11B, the pressure $p_0$ within enclosed space is greater than or equal to $p_{amb}$, and surface 551 of pad 550 is disengaged from interior end 545 of port 542. Thus, in this exemplary implementation of wound therapy apparatus 500, surface 551 of pad 550 alters between biased engagement with interior end 545 of port 542 when fluid is being evacuated from enclosed space 517 through port 542 at first stage of operation 505, and disengagement from interior end 545 of port 542 when either no fluid is being evacuated from enclosed space 517 or fluid is being input through port 542 at second stage of operation 510. Evacuation of output fluid 563 by suction through port 542 draws pad 550 into biased engagement with interior end 545 of port 542 then allowing exudate 561 to be evacuated from pad 550 through port 542, as illustrated in FIG. 11A. When suction at port 542 ceases, pad 550 is released from engagement with interior end 545 of port 542, as illustrated in FIG. 11B.

Figure 12:
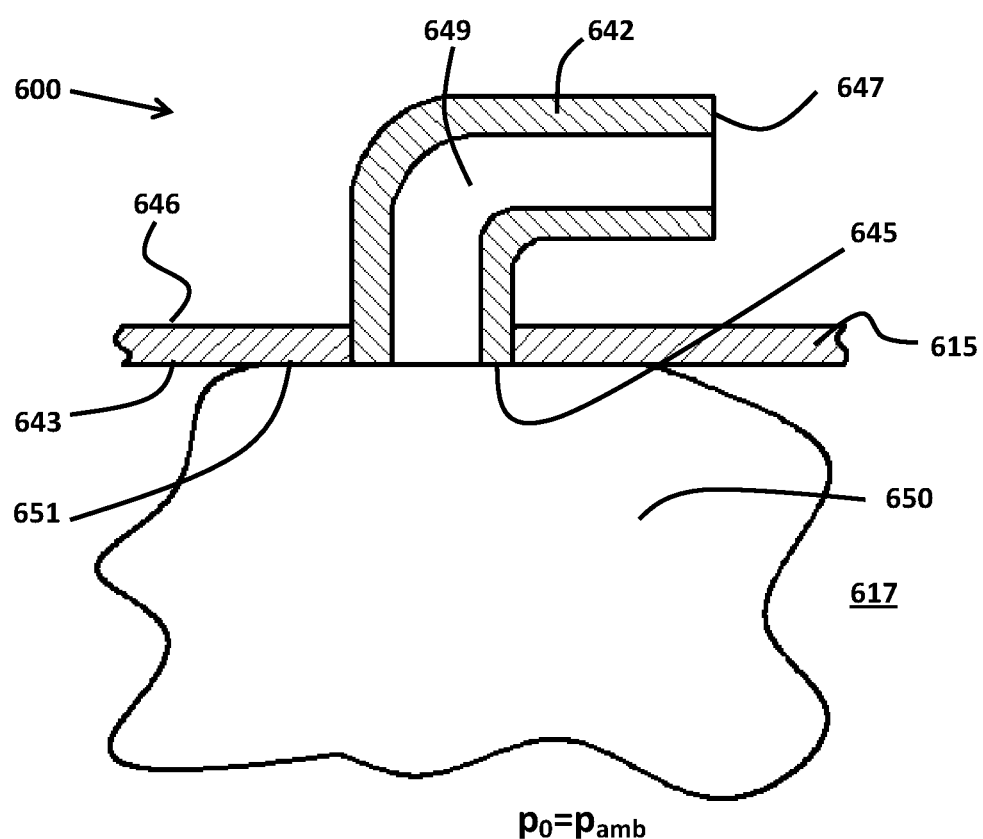
FIG. 12 illustrates by cross-sectional view portions of an eighth exemplary implementation of a wound therapy apparatus.

As illustrated in FIG. 12, exemplary wound therapy apparatus 600 includes wound interface 615 with inner surface 643 and outer surface 646 with inner surface 643 defining enclosed space 617. Pad 650 is disposed within enclosed space 617, as illustrated, and port 642 forms lumen 649 between interior end 645 and exterior end 647 of port 642. Lumen 649 passes through wound interface between inner surface 643 and outer surface 646. As illustrated in FIG. 12, the pressure $p_0$ within enclosed space generally equals $p_{amb}$ and no suction is being applied to port 642 to evacuate fluid from enclosed space 617. In contrast to exemplary wound therapy apparatus 500, which is illustrated in FIGS. 11A and 11B, side 651 of pad 650 remains biased against interior end 645 of port 642, as illustrated in FIG. 12. Thus, in this implementation, side 651 is in biased engagement with interior end 645 of port 642 during evacuation of fluid from enclosed space 617 as well as during cessation of evacuation of fluid from enclosed space 617 through port 642 or even during input of fluid into enclosed space through port 642.

Figure 13A:
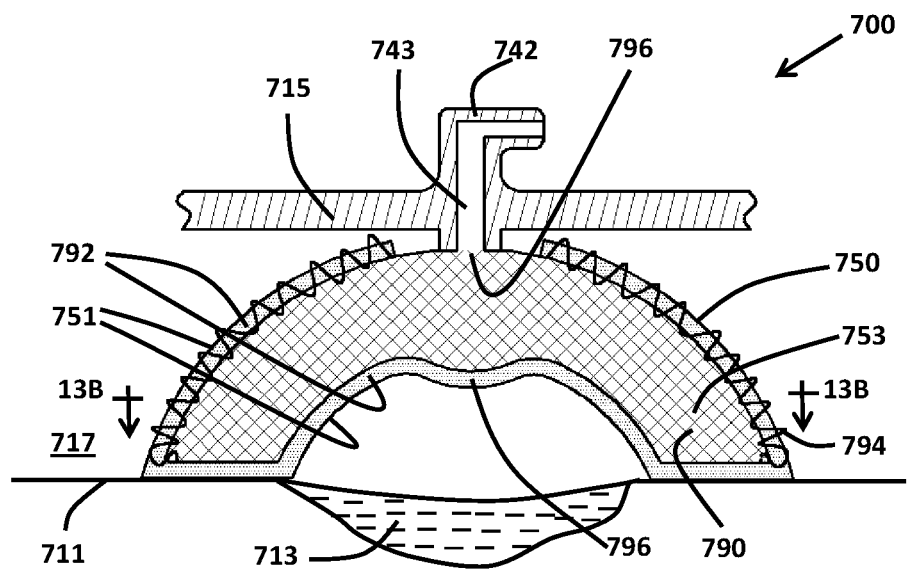
FIG. 13A illustrates by cross-sectional view portions of a ninth exemplary implementation of a wound therapy apparatus.
Figure 13B:
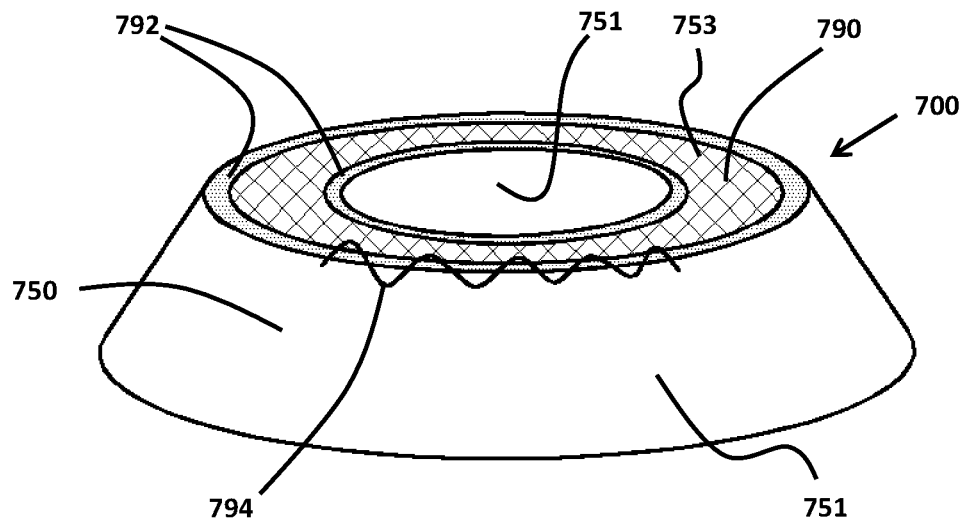
FIG. 13B illustrates by cross-sectional perspective view portions of the exemplary implementation of the wound therapy apparatus of FIG. 13A.

FIGS. 13A, 13B, illustrates exemplary wound therapy apparatus 700. As illustrated in FIG. 13A, enclosed space 717 is defined by wound interface 715 of wound therapy apparatus 700, and pad 750 is disposed within enclosed space 717 in fluid communication with lumen 743 of port 742. Pad 750, as illustrated in FIGS. 13A, 13B, is formed as a woven composite of synthetic fibers that may include a hydrophobic fiber 792, a hydrophilic fiber 790, and an elastomeric fiber 794.

Various knitting weaves can be deployed to hold the fibers 790, 792, and 794 together. In one implementation, a simple jersey-knit is used to create a bi-layer structure with one layer that is predominantly hydrophilic fiber 790 and the other layer of predominantly hydrophobic fibers 792. This structure may then be folded upon itself and stitched at the open perimeter to create pad 750 that is predominantly hydrophobic fibers 792 proximate the surface 751 of pad 750 and predominantly hydrophilic fibers 790 within the interior 753 of pad 750, as illustrated in FIG. 13B. The hydrophobic fibers 792 force exudate including other liquids from surface 751 onto the hydrophilic fibers 790 in interior 753. The exudate may be retained by hydrophilic fibers 790 and transferred through hydrophilic fibers 790 to lumen 743 of port 742 for withdrawal from enclosed space 717 by suction pressure applied to lumen 743.

In FIG. 13A, pad 750 takes the form of an inverted bowl that is positioned over the wound bed 713. Pad 750 may not directly contact the wound bed except during certain stages of operation of wound therapy apparatus 700 when pressure $p_0$ within enclosed space 717 is sufficiently negative to draw the wound bed into contact with pad 750. When wound bed 713 is in contact with pad 750, exudate from wound bed 713 may be transferred from wound bed 713 to pad 750, through pad 750, and from pad 750 through port 742. Pad 750 may optionally have region 796 that is at least in intermittent contact with port 742, that does not have, or has very little, hydrophobic fibers 792 at region 796 of surface 751. Pad 750 may additionally have different weave content in different regions of pad 750 for specific applications. For example, having a predominantly hydrophobic fiber 792 at a portion of surface 751 will decrease amount of moisture at the surface 751, and, hence, the likelihood of skin maceration from prolonged wet contact with this portion of surface 751. Pad 750 may be replaceably and removably deployed in wound interface 715 or pad 750 may be fixedly engaged with wound interface 715, in various implementations.

Figure 14:
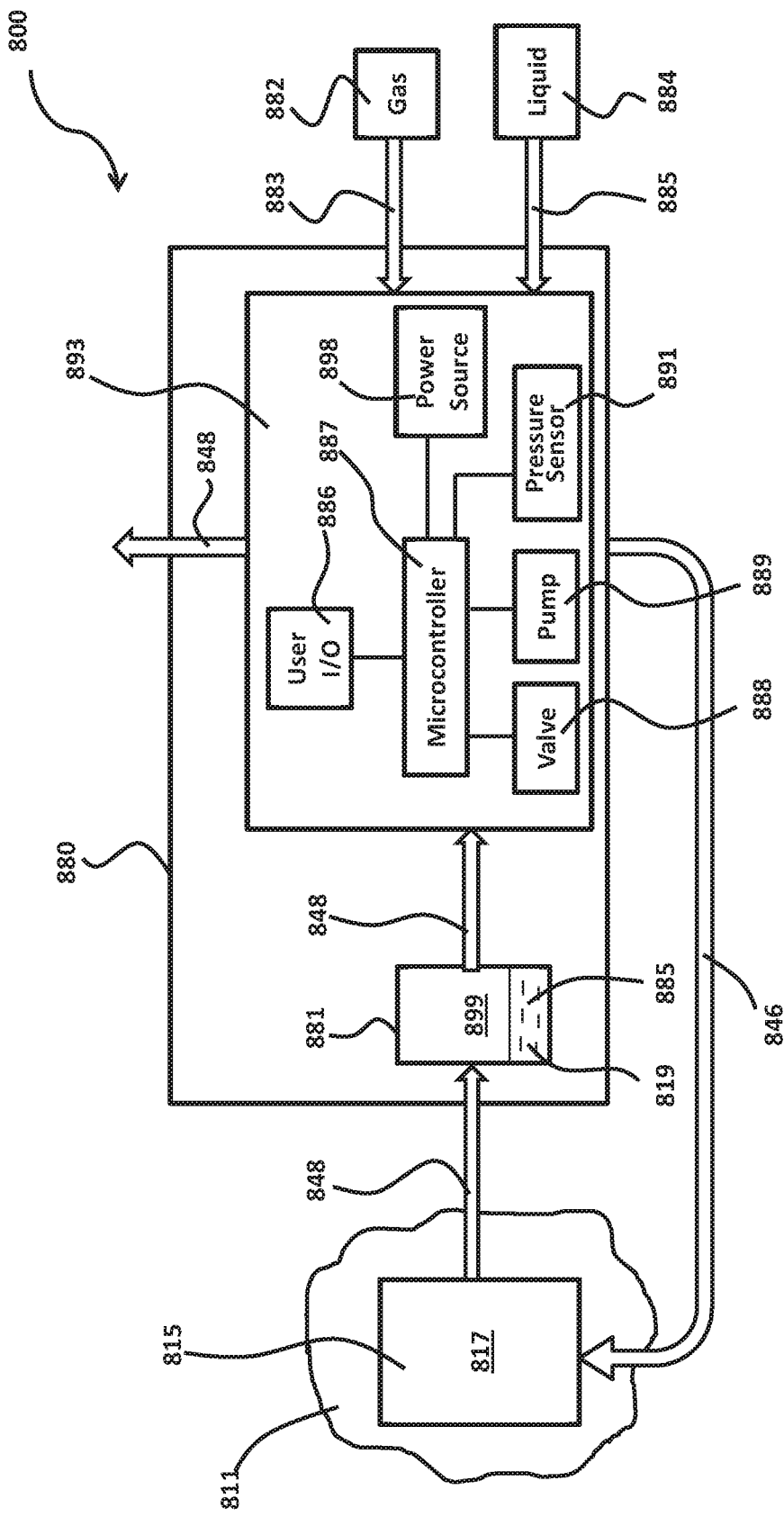
FIG. 14 illustrates by schematic diagram a tenth exemplary implementation of a wound therapy apparatus; and, FIG. 15 illustrates by process flow chart an exemplary method of use of the wound therapy apparatus.

FIG. 14 illustrates exemplary wound therapy apparatus 800. As illustrated in FIG. 14, wound therapy apparatus 800 includes gas source 882 and liquid source 884 in fluid communication with control module 880, and control module 880 is in fluid communication with wound interface 815. Wound interface 815 is secured to skin surface 811 to define enclosed space 817 over a wound bed, such as wound bed 13, 113, 213, 313, 413, 713 1013, as illustrated. Wound interface 815 may be formed, for example, similarly to wound interface 15, 115, 215, 315, 415, 515, 615, 715, 1015 and enclosed space 817 may be similar to enclosed space 17, 117, 217, 317, 417, 517, 617, 717, 1017, respectively. Control module 880 may monitor various parameters within the enclosed space 817 such as pressure $p_0$, and control module 880 may interact with such parameters to deliver various therapies.

Control module 880, in this implementation, includes control group 893 and canister 881, and control group 893 includes microcontroller 887 in operative communication with power source 898, user I/O 886, valve 888, pump 889, and pressure sensor 891 to control or monitor the operation of power source 898, valve 888, pump 889, pressure sensor 891, at least in part in response to the user inputs via user I/O 886. Microcontroller 887 may include, for example, a microprocessor, memory, A/D converter, D/A converter, clock, I/O connectors, and so forth, and microcontroller 887 may be configured, for example, as a single chip or as chip set mounted on a board, as would be readily recognized by those of ordinary skill in the art upon study of this disclosure.

Power source 898 may be, for example, mains electric or battery, and power source 898 may include, for example, a transformer, inverter, rectifier, or voltage filter. Valve 888 and pressure sensor 891 may be representative of various numbers and configurations of valves and various numbers and configurations of pressure sensors, respectively, in this illustration. Various communication pathways may be disposed about control module 880 to communicate electrical power from power source 898 to microcontroller 887, valve 888, pump 889, and pressure sensor 891.

User I/O 886 may include various switches, push buttons, dials, and so forth, whether virtual or physical for obtaining user inputs that are then communicated to microcontroller 887 in order to allow the user to direct the operation of wound therapy apparatus 800. Various communication pathways such as electrical, electromagnetic (e.g. Bluetooth), optical (e.g. LASER, IR), and networked communications may be employed for communication between microcontroller 887 and user I/O 886. Microcontroller 887 controls the operation of wound therapy apparatus 800 including control module 880 based, at least in part, upon user inputs communicated to microcontroller 887 from user I/O 886. Microcontroller 887 may communicate date to user I/O 886 indicative of the operation of wound therapy apparatus 800, and user I/O 886 may display this data to the user. User I/O 886 may be located in proximity to microcontroller 887, in some implementations, and user I/O 886 may be, at least in part, remotely located from and in network communication with microcontroller 887.

As illustrated in FIG. 14, gas source 882 fluidly communicates gas 883 with control group 893 of control module 880, and liquid source 884 fluidly communicates liquid 885 with control group 893 of control module 880. Control group 893 of control module 880 as controlled by microcontroller 887 is operable to select input fluid 846 as gas 883 from gas source 882, liquid 885 from liquid source 884, or a combination of gas 883 from gas source 882 and liquid 885 from liquid source 884. Input fluid 846 is input into enclosed space 817 as controlled by control group 893 of control module 880. Input fluid 886 may be, for example, equivalent to input fluid 78, 178.

Control group 893 of control module 840 as controlled by microcontroller 887 is operable to control the flow of input fluid 846 from control module 880 to enclosed space 817 of wound interface 815, the flow of output fluid 848 from enclosed space 817 of wound interface 815 to control module 880, and the exhausting of at least portions of output fluid 848 into the ambient environment, in this implementation, using valve 888, pump 889, and pressure sensor 891. Output fluid 848 may be, for example, equivalent to output fluid 76, 176, 563.

By controlling the flow of input fluid 846 into enclosed space 817 and the withdrawal of output fluid 848 from enclosed space 817, control module 880 may cycle the pressure $p_0$ within enclosed space 817, for example, over a pressure range $p_{min} \leq p_0 \leq p_{max}$. Valve 888 may include one or more valves disposed about control module 880 and operable, for example, to select input fluid 846 as either gas 883 from gas source 882 or liquid 885 from liquid source 884, to control the flow of input fluid 846 from control module 880 into enclosed space 817 of wound interface 815, and to control the flow of output fluid 848 withdrawn from enclosed space 817 of wound interface 815 to control module 880. Pressure sensor 891 may include at least one or more pressure sensors operable, for example, to monitor pressure at various locations in gas 883, liquid 885, input fluid 846, output fluid 848, or pressure $p_0$ within enclosed space 817 of wound interface 815. Microcontroller 887 may alter the operation of valve 888 or pump 889 in response to signals from pressure sensor 891. Input fluid 846 may be communicated under pressure at gas source 882 or liquid source 884, and pump 889 may be used to convey output fluid 848 from enclosed space 817 through canister 881 for rejection into the ambient environment.

Wound therapy apparatus 800 may include various fluid conveyances, for example hoses, pipes, valves, tubing, connectors, pressure regulators, and various other fittings, to communicate gas 883 and liquid 885 from gas source 882 and liquid source 884, respectively, to control module 880 and to communicate input fluid 846 and output fluid 848 between enclosed space 817 of wound interface 815 and control module 880.

Output fluid 848 passes through canister 881 as output fluid 848 is returned to control module 880 following withdrawal from enclosed space 817 of wound interface 815, and exudate 819 or liquid, such as liquid 885, from fluid 848 is captured from output fluid 848 in chamber 899 of canister 881. Gaseous portions of output fluid 848 or gas displaced from chamber 899 of canister 881 by capture of exudate or liquid within chamber 899 may then be discharged to the ambient environment from control module 880, as illustrated.

In operation, wound therapy apparatus, such as wound therapy apparatus 10, 100, 200, 300, 400, 500, 600, 700, 800, 1000 is used to treat a wound bed, such as wound bed 13, 113, 213, 313, 413, 713 1013 within a enclosed space, such as enclosed space 17, 117, 217, 317, 417, 517, 617, 717, 817, 1017 that is fluid tight and encloses the wound bed at the skin surface. The wound interface, such as wound interface 15, 115, 215, 315, 415, 515, 615, 715, 815, 1015 of the wound therapy apparatus is secured to the skin surface, such as skin surface 11, 111, 211, 311, 411, 711, 811, 1011 around the wound bed so that at least portions of the wound bed proximate the skin surface lie within the enclosed space. Various adhesives may be applied to the skin surface around the wound bed to protect the skin surface or to secure the portions of the wound therapy apparatus to the skin surface. Following securement to the skin surface about the wound bed, fluid may be evacuated from the enclosed space through a port, such as port 42, 142, 242, 342, 442, 542, 642, 742, 1003 that fluidly communicates with the enclosed space, and fluid may be input into the enclosed space either through the port or through a second port, such as port 44, 144, 244, that fluidly communicates with the enclosed space in order to periodically vary the pressure $p_0$ within the enclosed space over a pressure range $p_{min} \leq p_0 \leq p_{max}$ and $p_{max}$ may be greater than ambient pressure $p_{amb}$, maximum pressure $p_{max}$ may be generally equal to ambient pressure $p_{amb}$, or maximum pressure $p_{max}$ may be less than ambient pressure $p_{amb}$, in various implementations. The pressure range $p_{min} \leq p_0 \leq p_{max}$ may change over the course of wound therapy.

Periodically varying pressure $p_0$ within the enclosed space may massage the wound bed and surrounding tissue by alternately distending the wound bed into the enclosed space, and releasing the wound bed from distention back to a baseline state, which may palpate the vascular system proximate the wound bed thereby increasing blood flow to the wound bed. The resultant surges in blood flow proximate the wound bed to may promote healing of the wound bed. Massaging of the wound bed may promote the emanation expulsion of exudate from the wound bed. It should be noted that distension of wound bed into enclosed space usually does not begin as soon as $p_0$ becomes less than $p_{amb}$ but as pressure $p_0$ becomes sufficiently less than $p_{amb}$.

A control module, such as control module 880 may control the input of fluid into the enclosed space and the withdrawal of fluid from the enclosed space, and the fluid may include liquid, gas, or mixtures of liquid and gas. Various liquids, gas(ses), and combinations of liquids and gas(ses) may be input into the enclosed space and the liquids, gas(ses), and combinations of liquids and gas(ses) may change over the course of wound therapy.

A pad, such as pad 50, 150, 450, 550, 650, may be disposed within the enclosed space to absorb exudate from the wound bed. Periodically varying the pressure $p_0$ and corresponding distention of the wound bed into the enclosed space from a baseline state into a distended state and release of the wound bed from the distended state to the baseline state may alternately bring the wound bed into contact with the pad to communicate exudate from the wound bed into the pad, and remove the wound bed from contact with the pad to prevent integration of the pad with the wound bed. Various gaseous fluids may be input into the enclosed space or evacuated from the enclosed space via the port or the second port as the pressure $p_0$ is periodically varied. Exudate may be evacuated from the enclosed space via the port that communicates fluidly with the pad. Exudate may be captured in a canister of a control module, such as canister 881.

The wound bed may be observed within the enclosed space through a cover, such as cover 40, 140, 240, 340, 440, which may be formed, at least in part, of a transparent material. Windows, such as windows 139a, 139b, 139c, 139d, may be provided about the wound therapy apparatus to allow observation of the wound bed within the enclosed space. In various implementations, the cover may be positioned between an open position, such as open position 46, and a closed position, such as closed position 48, either to allow direct intervention into the enclosed space including the wound bed or to sealingly enclose the enclosed space, respectively.

Dressing may be omitted from the wound bed, at least during portions of the healing process. The absence of constant dressing contact with the wound bed may allow use of the wound therapy apparatus throughout to even the final stage of healing of the wound bed, and may allow viewing of the wound bed though the wound interface. Portions of the wound therapy apparatus such as the pad or the entirety of the wound therapy apparatus may be replaced as required during the healing process. The wound therapy apparatus is removed upon healing of the wound bed.

Figure 15:
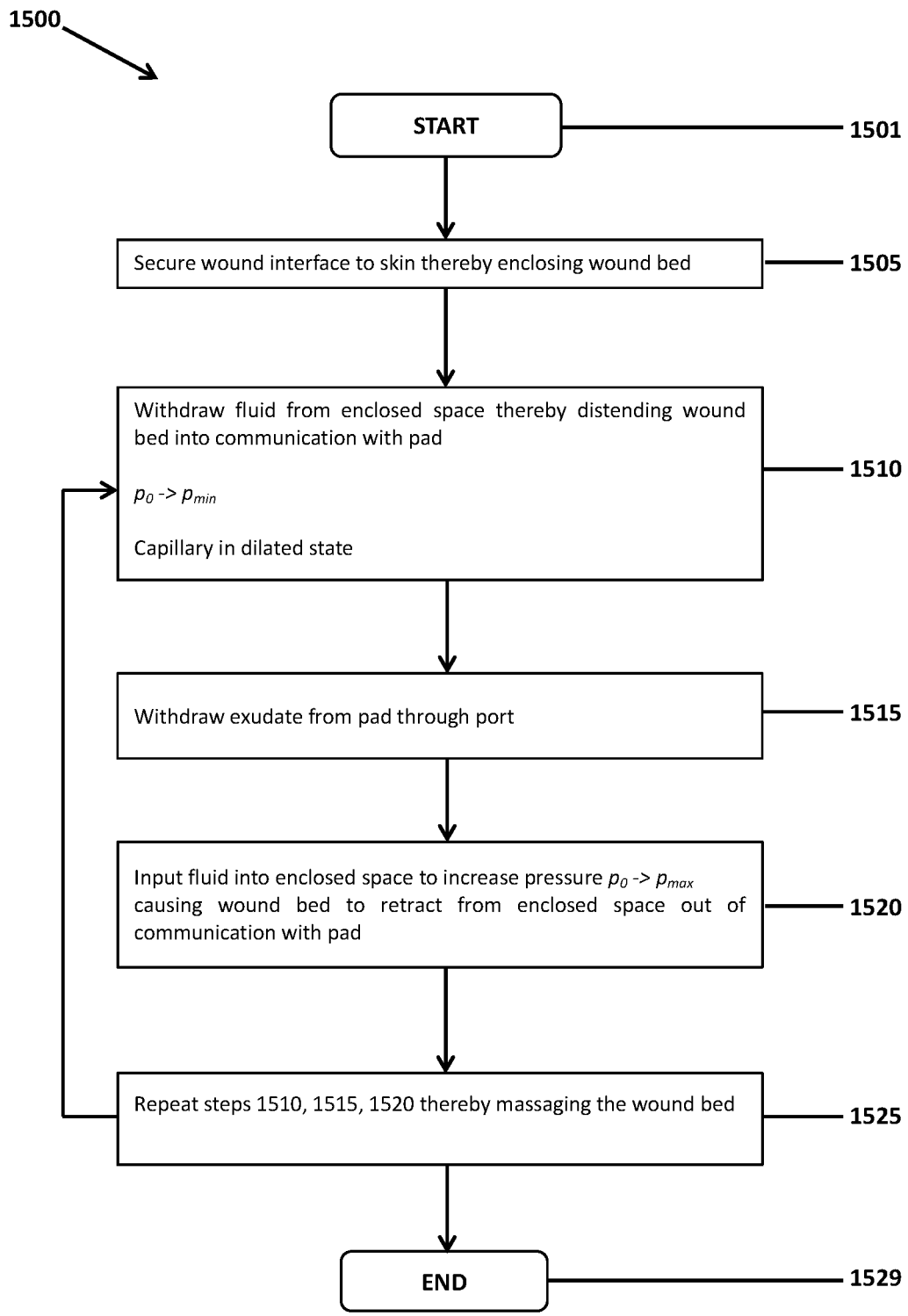

An exemplary method 1500 of use of the wound therapy apparatus disclosed herein is presented in FIG. 15. Method 1500 is entered at step 1501. At step 1505, the wound interface is secured to the skin thereby enclosing wound bed by an enclosed space.

At step 1510, fluid is withdrawn from the enclosed space thereby distending wound bed into communication with a pad disposed within the enclosed space. Exudate may be withdrawn from the wound bed into the pad. The pressure is decreased $p_0 \rightarrow p_{min}$ and the capillaries proximate the wound bed are placed in a dilated state.

At step 1515, exudate is withdrawn from the pad through the port. Periodic suction may be applied to withdraw the exudate from the pad.

As step 1520, fluid is input into enclosed space to increase pressure $p_0 \rightarrow p_{max}$ causing wound bed to retract from enclosed space and out of communication with pad. The fluid input at step 1520 may be either liquid or gas and, if gas, may have an oxygen concentration greater than that of atmospheric air (greater than 20.95% by volume).

At step 1525, steps 1510, 1515, 1520 are repeated thereby massaging the wound bed. Steps 1510, 1515, 1520 may be repeated over a time period of, for example, about 5 minutes or about 6 minutes. Exemplary method 1500 terminates at step 1529.

Accordingly, methods of use of the wound therapy apparatus may include the step of securing sealingly a wound interface to the skin surface around a wound bed to form a enclosed space that is fluid-tight and enclosing the wound bed at the skin surface with the wound interface being sufficiently deformation resistant to maintain a enclosed space within to accommodate distention of at least a portion of the wound bed into the enclosed space when the pressure $p_0$ within the enclosed space is sufficiently lower than ambient pressure $p_{amb}$. Methods of use may include the step of absorbing exudate from the wound bed using a pad disposed about the enclosed space, and the step of withdrawing exudate from the pad via a port disposed about the wound interface. Methods of use may include the step inputting fluid (gas or liquid) into the enclosed space via a port and then alternatingly, removing the fluid by the port. Methods of use may include the step inputting fluid (gas or liquid) into the enclosed space via a port and withdrawing the liquid via a second port. Methods of use may include the step varying the pressure $p_0$ within the enclosed space sufficiently to distend rhythmically at least a portion of the wound bed into the enclosed space cavity, which may produce surges in blood flow and micro-deformation of the wound bed beneficial for healing. Methods of use may include the step of distending the wound bed into communication with a pad for exudate removal from the wound bed and then releasing the wound bed from communication with the pad. Methods of use may include the step of securing the wound interface sealingly conformably to the skin surface around the wound bed using an annular cushion biased against the skin surface around a wound. Methods of use may include the step of securing the wound interface sealingly conformably to the skin surface around the wound bed using an apron disposed about the wound interface. Methods of use may include the step of positioning a cover portion of the wound interface between a sealing position and an open position thereby allowing direct intervention to the enclosed space. Methods of use may include the step of viewing the wound bed through a transparent portion of the wound interface. Methods of use may include the step of selecting the use or non-use of a pad or dressing in relation to the wound bed. Methods of use may include the step of distributing pressure $p_0$ within the enclosed space evenly over the wound bed thereby reducing uneven pressure gradient that may result in decreased blood flow proximate the wound boundary. Methods of use may include the step of delivering of a range of other therapeutics including various liquids and gases under a range of pressures from positive to negative, and incubation of bioengineered materials such as tissue stroma or skin grafts. Methods of use may include the step of using said wound therapy apparatus in a myriad of feasible ways in human or veterinary applications to treat conditions ranging from acute and chronic wounds, prevention of surgical site infections and enhancing a higher chemotherapeutic response rate.

While the preceding discussion has focused on wound care, the wound therapy apparatus disclosed herein may have useful applications in other areas of both human and veterinary medicine. As an example, in chemotherapy for cancer treatment, many of the drugs are not sufficiently selective to only kill tumor cells. However, by selectively elevating the metabolism of tumor cells, it is possible to achieve a higher kill rates during the time chemotherapeutics are being delivered. One effective way to raise the metabolic rate is to increase the body temperature, but it is both impractical and deleterious to raise total body temperature, akin to having a raging fever. However, at least for the treatment of relatively superficial tumors such as skin and breast cancers, it is entirely feasible to place an appropriately shaped and sized wound interface over the tumor site, and concomitant with chemotherapy, infuse very warm liquid (for example, 42° C. or 107° F.) that is much higher in temperature than is attained in the highest of clinical fevers. The resultant kill rate should be higher for tumors that have been subjected to this local hyperthermia while chemotherapeutic agent is circulating.

The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only. The Abstract is not intended to identify key elements of the apparatus and related methods of use disclosed herein or to delineate the scope thereof. Upon study of this disclosure and the exemplary implementations herein, one of ordinary skill in the art may readily recognize that various changes, modifications and variations may be made thereto without departing from the spirit and scope of the inventions as defined in the following claims.

The invention claimed is:

1. A wound therapy apparatus, comprising:
a wound interface that is sealingly securable to a skin surface surrounding a wound bed to form an enclosed space over the wound bed that is fluid-tight;
an interstice formed by a bifurcation of the wound interface into a distal side and a proximal side, the distal side being essentially rigid to maintain essentially a shape in three dimensions of the distal side under a variation of a pressure ($p_0$) between a minimum pressure ($p_{min}$) and a maximum pressure ($p_{max}$) of a wound therapy within the enclosed space, the interstice being between the distal side and the proximal side, and the distal side being interposed between the interstice and the enclosed space to separate the interstice from the enclosed space;
a pad to absorb exudate from the wound bed, the pad received within the interstice;
several passages being disposed through the distal side to communicate a fluid between the enclosed space and the interstice;
a port disposed on the wound interface to fluidly communicate with the interstice;
and wherein said wound therapy apparatus is adapted to displace the wound bed proximally towards the distal side in response to the variation of the pressure ($p_0$) within the enclosed space.

2. The apparatus of claim 1, wherein at least portions of the distal side are adapted to bias periodically against the wound bed in response to the variation of the pressure ($p_0$) within the enclosed space.

3. The apparatus of claim 1, wherein the shape is configured as a convex surface with respect to the wound bed.

4. The apparatus of claim 1, further comprising:
the variation of the pressure ($p_0$) within the enclosed space is periodic within a pressure range of ambient pressure and about—150 mm Hg gauge.

5. The apparatus of claim 1, wherein a fluid communicated with the enclosed space through the port comprises a gas having an oxygen concentration greater than that of atmospheric air.

6. A wound therapy apparatus, comprising:
a wound interface sealingly securable to a skin surface around a wound bed to form an enclosed space over the wound bed that is fluid-tight, an entirety of a portion of the wound interface forming the enclosed space is of essentially rigid construction to maintain essentially a shape in three dimensions of the portion of the wound interface under a variation of a pressure ($p_0$) between a minimum pressure ($p_{min}$) and a maximum pressure ($p_{max}$) of a wound therapy;
a port disposed on the wound interface to communicate fluid with the enclosed space in order to vary the pressure ($p_0$) within the enclosed space
a pad disposed within the enclosed space to absorb exudate from the wound bed, a most distal portion of the pad always being proximal to the skin surface when the wound interface is sealingly secured to the skin surface; and
a position of the pad within the enclosed space, the position adapted to contact the pad with the wound bed when the pressure ($p_0$) is at the minimum pressure ($p_{min}$) and to release the pad from contact with the wound bed when the pressure ($p_0$) is at the maximum pressure ($p_{max}$).

7. The apparatus of claim 6, wherein the maximum pressure ($p_{max}$) is approximately equal to an ambient pressure ($p_{amb}$).

8. The apparatus of claim 6, wherein the port is in at least intermittent biased engagement with the pad to allow withdrawal of exudate from the pad.

9. The apparatus of claim 6, wherein the pad comprises more hydrophobic fibers than hydrophilic fibers on a distal surface of the pad to convey exudate away from the wound bed and more hydrophilic fibers than hydrophobic fibers within an interior of the pad to transfer exudate from the distal surface through the pad to the port.

10. The apparatus of claim 6, wherein the pad comprises a material selected from polyvinyl alcohol, polyurethane, aliphatic polyamide fiber, semi-aromatic polyamide fiber, or polyester fiber.

11. The apparatus of claim 6, further comprising:
an interstice formed within an interior of the wound interface by a bifurcation of the wound interface into a distal side and a proximal side the distal side being essentially rigid, the distal side being interposed between the interstice and the enclosed space to separate the interstice from the enclosed space with the interstice being between the distal side and the proximal side,
the pad disposed within the interstice with a distal surface of the pad enclosed by the distal side; and several passages disposed through the distal side for fluid communication between the enclosed space and the interstice.

12. The apparatus of claim 6, the pad is replaceably receivable by the wound interface.

13. The apparatus of claim 6, the wound interface further comprising:
a cover positionable between a sealing engagement position and an open engagement position that allows direct intervention into the enclosed space.

14. The apparatus of claim 6, wherein the wound bed is viewable through a transparent portion of the wound interface.

15. The apparatus of claim 6, the wound interface further comprising:
a cushion that forms a closed annular circumference, the cushion comprising an inflatable sac or closed-cell foam, and the cushion adhesively and sealingly securable to the skin surface to sealingly secure the wound interface to the skin surface.

16. The apparatus of claim 6, the wound interface further comprising:
an apron that extends forth radially from portions of said wound interface that define the enclosed space to form a closed perimeter for conformable and sealing securement of the wound interface to the skin surface.

17. The apparatus of claim 6, the wound interface further comprising:
a flange disposed about an outer surface of the wound interface at a distal end to sealingly and conformably secure the wound interface to the skin surface, the flange operable to distribute over the skin surface forces from pressure ($p_0$) within the enclosed space.

18. The apparatus of claim 6, wherein the wound interface is sealingly securable to an ovoid or an elongated shaped region of skin surface around the wound boundary of the wound bed.

19. The apparatus of claim 6, wherein ($p_{min}$) is selected to increase blood flow in capillaries above a baseline.

20. The apparatus of claim 6, wherein a periodic variation of the pressure ($p_0$) within the enclosed space between a minimum pressure ($p_{min}$) and a maximum pressure ($p_{max}$) is selected to promote oxygenation of the wound bed.

21. A wound therapy apparatus, comprising:
a wound interface sealingly securable to a skin surface around a wound bed with a portion of the wound interface forming an enclosed space over the wound bed that is fluid-tight, the portion of the wound interface is of essentially rigid construction to maintain essentially a shape in three dimensions of the portion of the wound interface under a variation of a pressure ($p_0$) between a minimum pressure ($p_{min}$) and a maximum pressure ($p_{max}$) of a wound therapy;
a port disposed on the wound interface to communicate fluid with the enclosed space in order to alter the pressure ($p_0$) within the enclosed space over a time period
a pad received within the enclosed space to absorb exudate emanating from the wound bed; and
a position of the pad within the enclosed space, the position adapted to alter a biased engagement of the pad with the wound bed as the pressure ($p_0$) varies between the minimum pressure ($p_{min}$) and the maximum pressure ($p_{max}$) with a most distal portion of the pad being proximal to the skin surface.

22. The wound therapy apparatus of claim 21 wherein the time period is less than or equal to 6 minutes.

23. The wound therapy apparatus of claim 21, the maximum pressure ($p_{max}$) is greater than an ambient pressure ($p_{amb}$).

* * * * *